(12) United States Patent
Aldrich et al.

(10) Patent No.: US 8,809,278 B2
(45) Date of Patent: Aug. 19, 2014

(54) CYCLIC TETRAPEPTIDES

(75) Inventors: Jane V. Aldrich, Lawrence, KS (US); Nicolette C. Ross, Jupiter, FL (US); Santosh Kulkarni, Bangalore (IN)

(73) Assignee: University of Kansas, Lawrence, KS (US)

( * ) Notice: Subject to any disclaimer, the term of this patent is extended or adjusted under 35 U.S.C. 154(b) by 530 days.

(21) Appl. No.: 13/003,761

(22) PCT Filed: Jul. 10, 2009

(86) PCT No.: PCT/US2009/050263
§ 371 (c)(1),
(2), (4) Date: Apr. 21, 2011

(87) PCT Pub. No.: WO2010/006267
PCT Pub. Date: Jan. 14, 2010

(65) Prior Publication Data
US 2011/0190212 A1      Aug. 4, 2011

Related U.S. Application Data

(60) Provisional application No. 61/080,118, filed on Jul. 11, 2008.

(51) Int. Cl.
*A61K 38/00* (2006.01)
*A61K 38/12* (2006.01)
*C07K 5/00* (2006.01)
*C07K 5/12* (2006.01)

(52) U.S. Cl.
USPC ......... 514/21.1; 514/17.5; 514/17.6; 530/321

(58) Field of Classification Search
None
See application file for complete search history.

(56) References Cited

U.S. PATENT DOCUMENTS 5,216,124 A   6/1993   Hansen et al.
6,399,568 B1  6/2002   Nishino et al.

FOREIGN PATENT DOCUMENTS

WO   WO 2007/039058   4/2007
WO   WO 2008/057608   5/2008

OTHER PUBLICATIONS

Saito et al. 2002 "CJ-15208, a novel kappa opioid receptor antagonist from a fungus, ctenomyces serratus ATCC15502" J Antibiotics 55(10):847-854.*
Beardsley et al. 2005 "differential effects of the novel kappa opioid receptor antagonist, JDTic, on reinstatement of cocaine-seeking induced by footshock stressors vs cocaine primes and its antidepressant-like effects in rats" Psychopharmacology 183:118-126.*
Vig et al. 2004 "synthesis and opioid activity of side-chain-to-side-chain cyclic dynorphin A-(1-11) amide analogues cyclized between positions 2 and 5. 1. substitutions in position 3" J Med Chem 47:446-455.*

* cited by examiner

*Primary Examiner* — Jeffrey Stucker
*Assistant Examiner* — Adam M Weidner
(74) *Attorney, Agent, or Firm* — Workman Nydegger

(57) ABSTRACT

Cyclic tetrapeptides that are kappa opioid receptor (KOR) antagonists can be used in therapeutic applications for treating, inhibiting, and/or preventing drug addiction, drug use, or drug seeking behavior in a subject. This can include subjects that have a history of drug addiction. The drug can be selected from cocaine, alcohol, amphetamines, methamphetamines, nicotine, opiate, or combinations thereof. These cyclic tetrapeptides can also be useful for treating, inhibiting, and/or preventing stress-induced drug seeking behavior.

24 Claims, 9 Drawing Sheets

FIG. 7

| | JVA # | Compound | K$_i$ (nM +- SEM) | | | κ/μ/δ | Cyclase screen (% inhibition) | Comments |
|---|---|---|---|---|---|---|---|---|
| | | | κ | μ | δ | | | SEM for cyclase screen? |
| CJ-15,208 | | L-Trp Series | | | | | | |
| | 2801 [1] | [L-Trp] | 35.4 +- 3.6 (4) | 619 +- 87 (3) | 1200, 1050, 10000 R | 1/17.5 | -19% | R/δ |
| | 2803 | [Trp,Ala] | 8.03 +- 1.67 (4) | 32.1 +- 3.9 (3) | 8680 +- 1270 (3) | 1/4.0/1080 | -22% | |
| | 2804 | [Ala] | 1550 +- 290 (8) | 687 +- 81 (6) | >10000 (3) | 2.3/1/>14 | 14% | |
| | 2805 | [Ala,Trp] | 663 +- 220 (5) | 533 +- 28 (3) | >10000 (3) | 1.2/1/>15 | 25% | |
| | 2806 | [N-Me-D-Ala] | 113 +- 23 (5) | 140 +- 9 (3) | 1370 +- 70 (3) | 1/1.2/12.1 | 21% | |
| | 2807 | [Aib] | 339 +- 101 (5) | 1890 +- 180 (3) | 5690 +- 480 (3) | 1/5.6/16.8 | 9% | |
| | | D-Trp Series | | | | | | |
| | 2802 [1] | [D-Trp] | 30.6 +- 3.4 (5) | 259 +- 29 (3) | 2910 +- 1350 (3) R | 1/8.5 | -27% | R/δ |
| | 3003 | [S-Trp,Ala] | 3.15 +- 0.41 (3) | 27.3 +- 2.7 (3) | 8330 +- 1220 (3) | 1/8.7/2640 | -25% | |
| | 3002 | [D-Ala] | 1300 +- 60 (3) | 775 +- 71 (3) | >10000 (3) | 1.7/1/>12.9 | -15% | |
| | 3004 | [Ala, D-Trp] | 173 +- 4 (2) | 186 +- 3 (3) | >10000 (3) | 1/1.1/>57 | -6% | κ n = 1 |
| | 3001 | [D-N-MeAla,D-Trp] | 59.1 +- 5.1 (3) | 257 +- 14 (3) | 5690 +- 610 (3) | 1/4.3/96 | -2% | |

[1] K$_i$ (κ) in mouse brain (Jay Mclaughlin):
JVA-2801: 21.2 +- 5.6 nM (4)
JVA-2802: 46.9 +- 16.1 nM (4)

CYCLIC TETRAPEPTIDES

This invention was made with government support under Grant Number DA018832 awarded by the National Institute of Health. The government has certain rights in the invention.

CROSS-REFERENCE TO RELATED APPLICATIONS

This application is a U.S. Nationalization of PCT Application Number PCT/US2009/050263 filed Jul. 10, 2009, which claims the benefit and priority to U.S. Provisional Application No. 61/080,118 filed Jul. 11, 2008, the entireties of which are incorporated herein by reference.

BACKGROUND

The K-opioid receptor (i.e., kappa-opioid receptor) is a type of opioid receptor which binds the opioid peptide dynorphin as the primary endogenous ligand. The κ opioid receptors are widely distributed in the brain, spinal cord, and in pain neurons. Kappa opioid receptors have recently been investigated for their therapeutic potential in the treatment of addiction (Hasebe K, Kawai K, Suzuki T, Kawamura K, Tanaka T, Narita M, Nagase H, Suzuki T (October 2004) "Possible pharmacotherapy of the opioid kappa receptor agonist for drug dependence" *Annals of the New York Academy of Sciences* 1025: 404-13) and evidence points towards dynorphin, the endogenous kappa agonist, to be one of the body's natural addiction control mechanism (Frankel P S, Alburges M E, Bush L, Hanson G R, Kish S J (July 2008) "Striatal and ventral pallidum dynorphin concentrations are markedly increased in human chronic cocaine users" *Neuropharmacology* 55 (1): 41-6).

In experimental "addiction" models the kappa-opioid receptor has also been shown to influence stress-induced relapse to drug seeking behavior. For the drug dependent individual, risk of relapse is a major obstacle to becoming drug free. Recent reports demonstrated that kappa-opioid receptors are required for stress-induced reinstatement of cocaine seeking (Beardsley P M, Howard J L, Shelton K L, Carroll F I (November 2005) "Differential effects of the novel kappa opioid receptor antagonist, JDTic, on reinstatement of cocaine-seeking induced by footshock stressors vs cocaine primes and its antidepressant-like effects in rats" *Psychopharmacology (Berl.)* 183 (1): 118-26; Redila V A, Chavkin C (September 2008). "Stress-induced reinstatement of cocaine seeking is mediated by the kappa opioid system" *Psychopharmacology (Berl.)* 200 (1): 59-70; Blum K, Braverman E R, Holder J M, Lubar J F, Monastra V J, Miller D, Lubar J O, Chen T J, Comings D E (November 2000) "Reward deficiency syndrome: a biogenetic model for the diagnosis and treatment of impulsive, addictive, and compulsive behaviors" *Journal of psychoactive drugs* 32 Suppl: i-iv, 1-112).

It has also been reported that the dynorphin-Kappa opioid system is critical for stress-induced drug seeking. In animal models, stress has been demonstrated to potentiate cocaine reward behavior in a kappa opioid-dependent manner (McLaughlin J P, Marton-Popovici M, Chavkin C. (July 2003) "Kappa opioid receptor antagonism and prodynorphin gene disruption block stress-induced behavioral responses" *The Journal of Neuroscience* 23 (13): 5674-83; Mash, Deborah C. (June 2006) "Social defeat stress-induced behavioral responses are mediated by the endogenous kappa opioid system" *Neuropsychopharmacology* 31 (4): 787-94). These effects are likely caused by stress-induced drug craving that requires activation of the dynorphin/kappa opioid system. Although seemingly paradoxical, it is well known that drug taking results in a change from homeostasis to allostasis. It has been suggested that withdrawal-induced dysphoria or stress-induced dysphoria may act as a driving force by which the individual seeks alleviation via drug taking. The rewarding properties of the drug are altered, and it is clear kappa-opioid activation following stress increase its rewarding properties and cause potentiation of reward behavior, or reinstatement to drug seeking. The stress-induced activation of kappa-opioid receptors is likely due to multiple signaling mechanisms. The kappa-opioid receptors have marked effects on all types of addiction including alcohol and opiate abuse.

Cocaine addiction, as well as addiction to alcohol or other drug, is a world wide problem that has serious social, mental, and physical consequences. While various forms of prevention and/or treatment of addiction have been attempted, there remains a need for an improvement. For example, small molecules have been used as drugs to decrease the physical and/or mental conditions associated with addiction. However, many small molecules with bioactivity have negative side effects due to the ability of the small molecule to not only interact with the proper receptor(s) associated with addition (e.g., target receptors), but to also cross-interact with unintended receptors (e.g., non-target receptors).

SUMMARY

In one embodiment, the present invention is a method for antagonizing kappa-opioid receptors (KOR) present in tissue in vitro or in vivo, such as tissue in cell culture or living subject (e.g., human). The method can include administering at least one cyclic tetrapeptide KOR antagonist to the tissue in an amount sufficient to antagonize the KOR in the tissue, the cyclic tetrapeptide KOR antagonist can be an analog of CJ 15,208 which has the structure of Formula 1, or a derivative thereof. Formula 1 is shown below. In one aspect, the KOR antagonist is not Formula 1. In another aspect, the KOR antagonist is one of cyclo[D-Trp-Phe-D-Pro-Phe], cyclo[Trp-Ala-D-Pro-Phe], cyclo[D-Trp-Ala-D-Pro-Phe], or derivative thereof. In another aspect, the cyclic tetrapeptide KOR antagonist is cyclo[Trp-Ala-D-Pro-Phe], cyclo[D-Trp-Ala-D-Pro-Phe], or derivative thereof. Optionally, the cyclic tetrapeptide KOR antagonist can be selective for KOR over other opioid receptors. In another option, the cyclic tetrapeptide KOR antagonist can have at least about 3-fold more effectiveness compared to Formula 1.

In one embodiment, the cyclic tetrapeptide KOR antagonist can have substantial selectivity for KOR over other opioid receptors so as to inhibit negative side effects. For comparison, other opioid receptors can be MOR and DOR.

In one embodiment, the cyclic tetrapeptide KOR antagonist is administered to a subject in an effective amount sufficient to cross the blood brain barrier and antagonize the KOR to provide a therapeutic effect.

In one embodiment, the method can include administering a therapeutically effective amount of the cyclic tetrapeptide KOR antagonist to a subject having the tissue for treating, inhibiting, and/or preventing drug addiction, drug use, or drug seeking behavior in the subject. The method can further include identifying the subject to have a history of drug addiction. For example, the drug is selected from cocaine, alcohol, amphetamines, methamphetamines, nicotine, opiate, combinations thereof, or the like.

In one embodiment, the method can include administering a therapeutically effective amount of the cyclic tetrapeptide KOR antagonist to a subject having the tissue for treating, inhibiting, and/or prevention of drug seeking behavior. Such drug seeking behavior can be stress induced and/or related to a relapse.

In one embodiment, the method can include administering a therapeutically effective amount of the cyclic tetrapeptide KOR antagonist to a subject having the tissue for treating, inhibiting, and/or prevention of depression.

In one embodiment, the method can include administering a therapeutically effective amount of the cyclic tetrapeptide KOR antagonist to a subject having the tissue for treating, inhibiting, and/or prevention of anxiety.

In one embodiment, the present invention can include a method for agonizing kappa-opioid receptors (KOR) present in tissue in vitro or in vivo, such as tissue in cell culture or a living subject (e.g., human). Such a method can include administering at least one cyclic tetrapeptide KOR agonist to the tissue in an amount sufficient to agonize the KOR in the tissue, the cyclic tetrapeptide KOR agonist is CJ 15,208 which has a structure of Formula 1, or an analog of CJ 15,208, or a derivative thereof. In one aspect, the cyclic tetrapeptide KOR antagonist isn't Formula 1, or it can be. In one aspect, the cyclic tetrapeptide KOR agonist is one of cyclo[Trp-Phe-D-Pro-Phe], cyclo[Trp-Ala-D-Pro-Phe], cyclo[D-Trp-Ala-D-Pro-Phe], or derivative thereof.

In one embodiment, the method can include administering a therapeutically effective amount of a cyclic tetrapeptide KOR antagonist that has agonist activity to a subject having the tissue as an analgesic for treating, inhibiting, and/or prevention of pain.

In one embodiment, the present invention can include a cyclic tetrapeptide having KOR antagonist activity. The cyclic tetrapeptide KOR antagonist may not be CJ 15,208 having a structure of Formula 1, but may be an analog or derivative thereof. The cyclic tetrapeptide KOR antagonist can be one of cyclo[D-Trp-Phe-D-Pro-Phe], cyclo[Trp-Ala-D-Pro-Phe], cyclo[D-Trp-Ala-D-Pro-Phe], or derivative thereof. In one aspect, the cyclic tetrapeptide KOR antagonist can be cyclo[Trp-Ala-D-Pro-Phe], cyclo[D-Trp-Ala-D-Pro-Phe], or derivative thereof. In another aspect, the cyclic tetrapeptide is an analog of CJ 15,208 or derivative thereof having the structure of Scaffold 1, Scaffold 2, Scaffold 3, or Scaffold 4, which are shown below.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 3A is JVA-2801; FIG. 3B is JVA-2803; FIG. 3C is JVA-2802; and FIG. 3D is JVA-3003.

FIG. 7 illustrates the affinity of cyclic tetrapeptides for KOR, MOR, and DOR.

DETAILED DESCRIPTION OF THE PREFERRED EMBODIMENTS

Figure 1A:
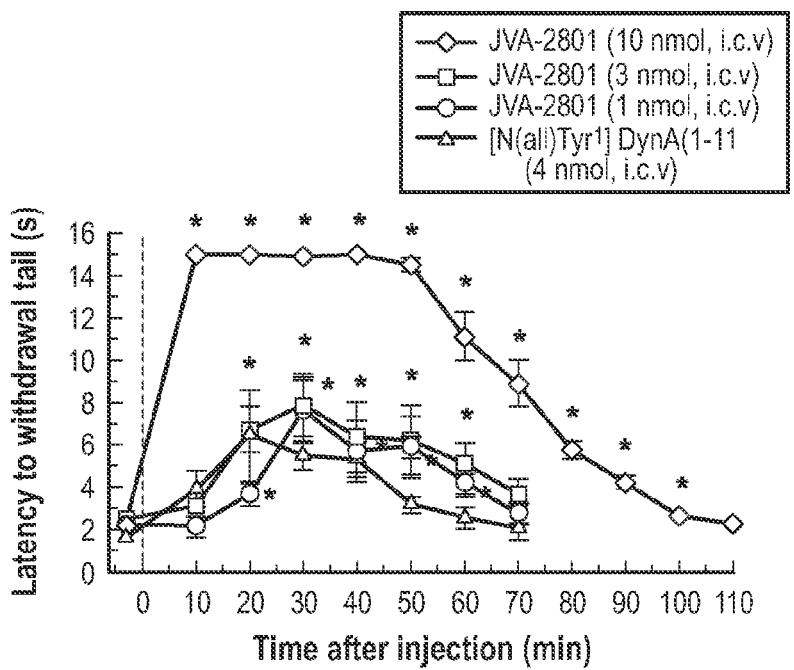
FIGS. 1A-1C illustrate agonist activity of JVA-2801 (FIG. 1A), JVA-2803 (FIG. 1B), and JVA-3003 (FIG. 1C) in the 55° C. warm water tail withdrawal assay following intracerebroventricular (i.c.v.) administration.

Generally, the present invention relates to cyclic tetrapeptides that have activity for antagonism of the kappa-opioid receptor. Some of the cyclic tetrapeptides have a dual action of antagonism of the kappa-opioid receptor and agonism. The cyclic tetrapeptides with kappa-opioid receptor antagonist activity can be used in treating, inhibiting, and/or preventing abuse of drugs, such as cocaine, methamphetamines, alcohol, and other. Also, the antagonists can be used for inhibiting drug-seeking behaviors, which includes stress-induced drug-seeking behaviors. Also, the present invention relates to specific cyclic tetrapeptides that can be administered in a therapeutically effective amount that crosses the blood-brain barrier so as to be active in the brain at kappa-opioid receptors, being either antagonistic or a dual KOR antagonist and agonist.

The ability of a kappa-opioid receptor (e.g., KOR) agonist to interact with the KOR has been contemplated as a biological process that may be used for pharmacological management of cocain addiction. However, it has recently been determined that a small molecule KOR antagonist can also be used in the pharmacological management of cocain addiction. Particularly, the ability of a small molecule to block the kappa-opioid receptor (e.g., KOR) as an antagonist (e.g., JDTic) has been shown to block stress-induced reinstatement of cocaine-seeking behavior has been published (Beardsley et al, Psychopharmacology, 2005, 183, 118-126). The peptide KOR antagonist arodyn also block stress-induced reinstatement of cocaine seeking behavior (Carey, Borozny, Aldrich, and McLaughlin, Eur. J. Pharmacol. 2007, 569, 84-89).

Numerous studies have demonstrated that KOR agonists (i.e., compounds that activate the receptors) can acutely block cocaine seeking behavior, but paradoxically chronic (i.e., long term) administration of KOR agonists has been reported to potentiate drug-seeking behavior. Thus, KOR antagonists (i.e., compounds that block the activity of agonists at the receptors) may be better suited for chronic treatment of drug abuse or stress-induced drug seeking behavior.

Generally, KOR antagonists are known to be useful in treatment of opiate addition and depression; however, many polypeptide KOR antagonists suffer from being unstable and unusable for systemic administration.

Recently, it has been shown that a cyclic tetrapeptide, CJ-15,208 and having Formula 1, can interact with opioid receptors (U.S. Pat. No. 5,885,959). CJ15,208 (i.e., cyclo[L-Trp-Phe-D-Pro-Phe] or cyclo[Trp-Phe-D-Pro-Phe]) is the natural product (see, U.S. Pat. No. 5,885,959; Saito et al., *Antibiot.* 2002, 55, 847-854). The interaction was indicated to provide analgesic activity, which can be attributed to being an agonist, and provide detoxication activity, which can be attributed to being an antagonist. Accordingly, the true functionality of CJ-15,208 was not properly characterized. It has now been found that CJ15,208 acts as an antagonist at kappa opioid receptors (KOR) in vivo and also has agonist activity. KOR antagonists have potential therapeutic uses as antidepressants, anti-anxiety agents, and for the treatment of opiate and cocaine addiction and other drug seeking behavior.

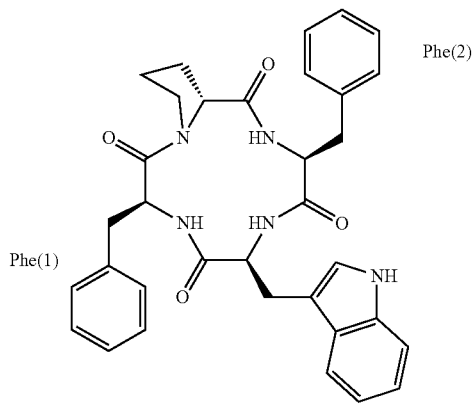

Formula 1: KOR antagonist, CJ 15,208 (cyclo[L-Trp-Phe-D-Pro-Phe]).

It has now been found that cyclic tetrapeptides that are analogs or derivatives of CJ-15,208 can be superiour antagonists of kappa-opioid receptors, and thereby can be useful as antidepressants, anti-anxiety agents, and for the treatment of opiate and cocaine addiction and other drug seeking behavior. Discussions of analogs or derivatives herein expressly exclude CJ-15,208. As used herein, "analogs" are considered to include R group substitutions of the amino acids to present a different amino acid in the cyclic tetrapeptide, where the R groups are shown below. Derivatives, are considered to include atom or substitutent exchanges such as one or more hydrogen atoms being substituted with an alkyl, halogen, hydroxy, amine, combinations thereof, or the like.

Accordingly, the present invention is a stable KOR antagonist in the form of a cyclic tetrapeptide that can be used in the prevention and/or treatment of cocaine addiction. The KOR antagonists are analogs of the cyclic tetrapeptide CJ-15,208 (cyclo[Trp-Phe-D-Pro-Phe]) which have similar or improved affinity for the target opioid receptors. Examples of the antagonists include cyclo[D-Trp-Phe-D-Pro-Phe] (Formula 2; Compound 2802), cyclo[Trp-Ala-D-Pro-Phe] (Formula 3; Compound 2803), and cyclo[D-Trp-Ala-D-Pro-Phe] (Formula 4; Compound 3003). Amino acids are considered to be L amino acids unless indicated to be D amino acids. It should be noted that CJ-15208 is also referred to as Compound 2801 with the L-Trp, and Compound 2802 is the D-Trp. With regard to the table showing the opioid activity, the L-Trp series is on the top, the D-Trp series is on the bottom. In both cases if one phenylalanine (e.g., clockwise from the L or D Trp) is replaced with alanine, there is a substantial increase in the infinity.

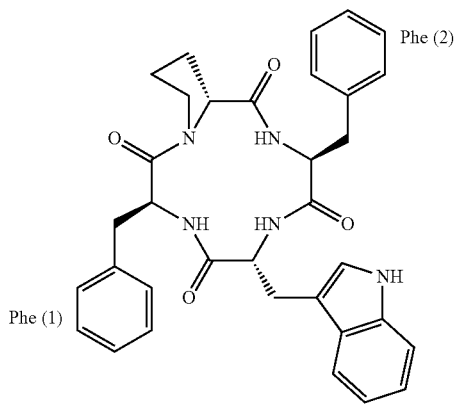

Formula 2 (Compound 2802)

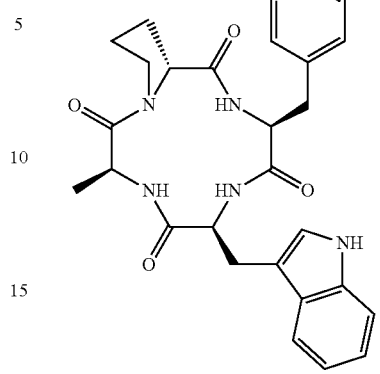

Formula 3 (Compound 2803)

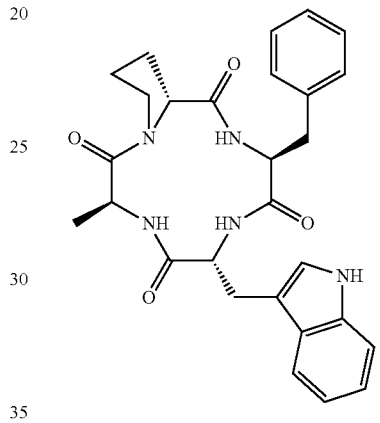

Formula 4 (Compound 3003)

The cyclic tetrapeptides are completely different in structure from known opioid ligands, which are either peptide or nonpeptide. The cyclic tetrapeptides lack a free N-terminal amine found in endogenous opioid peptide ligands. The cyclic tetrapeptides also lack basic amino acid residues typically found in peptides with high affinity for KOR. Interestingly changing the stereochemistry of the Trp residue, which is important for KOR binding, results in a new analog which retains KOR affinity comparable to the parent CJ-15,208, which is surprising and unexpected. In both CJ-15,208 and the D-Trp analog of CJ-15,208 (cyclo[D-Trp-Phe-D-Pro-Phe] (Formula 2; 2802)), substitution of Phe by Ala enhances affinity 4- to 10-fold. In contrast to linear peptides, the cyclic tetrapeptides are thought to be metabolically stable and exhibit enhanced membrane penetration (e.g. through the blood-brain barrier).

These KOR antagonists shown in Formulas 2-4 can be used in the prevention, inhibition, and/or treatment of drug abuse, specifically to treat, inhibit, and/or prevent stress-induced drug seeking behavior. Cyclic tetrapeptides can be metabolically stable, and can be active following systemic (e.g., subcutaneous, s.c., intravenous, i.v., or the like) administration. The cyclic tetrapeptide KOR antagonists can block stress-induced reinstatement of drug-seeking behavior following systemic administration.

It is thought that the cyclic tetrapeptide KOR antagonists will not have the pharmacokinetic problem associated with small molecule antagonists of KOR. Small molecule antagonists have exceptionally long activity in animal models (e.g., weeks to over a month after a single injection) that complicate their potential therapeutic use in humans. Cyclic tetrapeptides are expected to be shorter acting because of their metabolism by proteases even though the cyclic tetrapeptides have increased stability compared to linear peptides. By comparison, the cyclic tetrapeptides should have a longer halflife than other polypeptides, but also have a much shorter halflife than small molecule KOR antagonists. Unexpectedly, some of the cyclic tetrapeptides are more potent (14-fold) than CJ 15,208, see Table 1 below.

In one embodiment, the cyclic tetrapeptide KOR antagonists can be used for the treatment of drug abuse by blocking stress-induced reinstatement of drug-seeking behavior following systemic administration. Drugs included in this are at least cocaine, alcohol, methamphetamines, amphetamines, opioids (e.g., narcotic opioid alkaloids, morphine, codeine, heroin, oxycodone, hydrocodone, and any benzylisoquinoline alkaloid; synthetic opiates, fentanyl, meperidine and methadone), and the like. Accordingly, the cyclic tetrapeptides could be used as a prophylactic to prevent the onset of drug addiction rather than just to treat drug addiction. It is expected that the cyclic tetrapeptides may also be active in models for treatment of drugs of abuse other than cocaine, specifically opiates and amphetamine, and possibly others (e.g., alcohol and maybe even nicotine).

In one embodiment, the cyclic tetrapeptide KOR antagonists can be used to treat, inhibit, and/or prevent depression. Based on the activity of small molecule KOR antagonists, the cyclic tetrapeptides are expected to exhibit antidepressant activity. Similarly, the cyclic tetrapeptides can be used for treating, inhibiting, and/or preventing anxiety.

In one embodiment, the cyclic tetrapeptide KOR agonists can be used as analgesics. KOR agonists have previously been shown to have analgesic properties. As such, the cyclic tetrapeptide agonists can be used to treat, inhibit, and or prevent pain treatable by an analgesic.

The functionality of cyclic tetrapeptides was studied by preparing analogs of CJ-15,208, and testing the interactions with the opioid receptors. Some of the analogs were prepared by systematically replacing each amino acid individually with an alanine, and then testing for interactions with the opioid receptors. Usually, substitutions of amino acids with alanine can reveal a decrease in receptor activity, which shows a particular amino acid being important for binding. However, it has now been found that substitutions of amino acids in cyclic tetrapeptides actually increased the receptor interaction in a surprising and unexpected manner. The receptor interaction is shown in Table 1 below, which shows some of the cyclic tetrapeptides having increased receptor activity three to eight fold, three for one peptide and eight for the other.

The difference between the CJ-15208 and Compound 2802 cyclic tetrapeptides is the stereochemistry of the tryptophan. CJ-15208 has a L-Trp versus Compound 2802 having a D-Trp. Amino acid substitutions of the Phe that couples the L- or D-Trp and D-Pro can modulate KOR antagonist activity, wherein the Phe being substituted is clockwise-adjacent to the L or D Trp (e.g., see Formulas 1-4 showing CJ-15208 and Compound 2802 orientation). The cyclo[Trp-Ala-D-Pro-Phe] (ie., Compound 2803) or cyclo[D-Trp-Ala-D-Pro-Phe] (ie., Compound 3003) cyclic tetrapeptides are two examples of high affinity analogs which function as KOR antagonists. The data also indicates that the alanine of cyclo[Trp-Ala-D-Pro-Phe] (ie., Compound 2803) or cyclo[D-Trp-Ala-D-Pro-Phe] (ie., Compound 3003) can be replaced with a different amino acid in order to have an opioid antagonist with modulated receptor activity. That is, by substituting the alanine in these cyclic tetrapeptides with specific amino acids, KOR activity can be modulated as desired. Thus, cyclo[Trp-AA-D-Pro-Phe] or cyclo[D-Trp-AA-D-Pro-Phe], with AA being an amino acid other than Phe, can be KOR antagonists for use as described herein.

Additional examples of cyclic tetrapeptides in accordance with the present invention are shown in Table 2 below. In Table 2, the top row illustrates cyclic tetrapeptide analog scaffolds, and the columns show the R1, R2, R3, or R4 for the corresponding analog scaffold.

TABLE 2

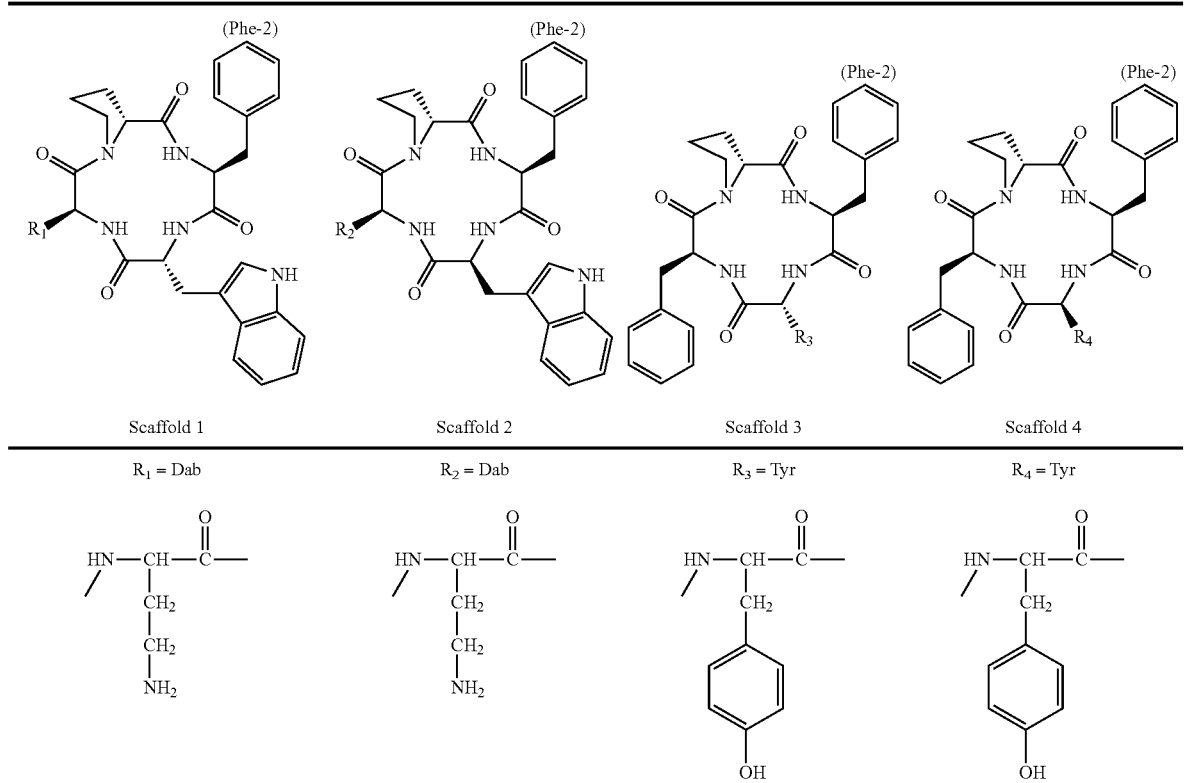

TABLE 2-continued
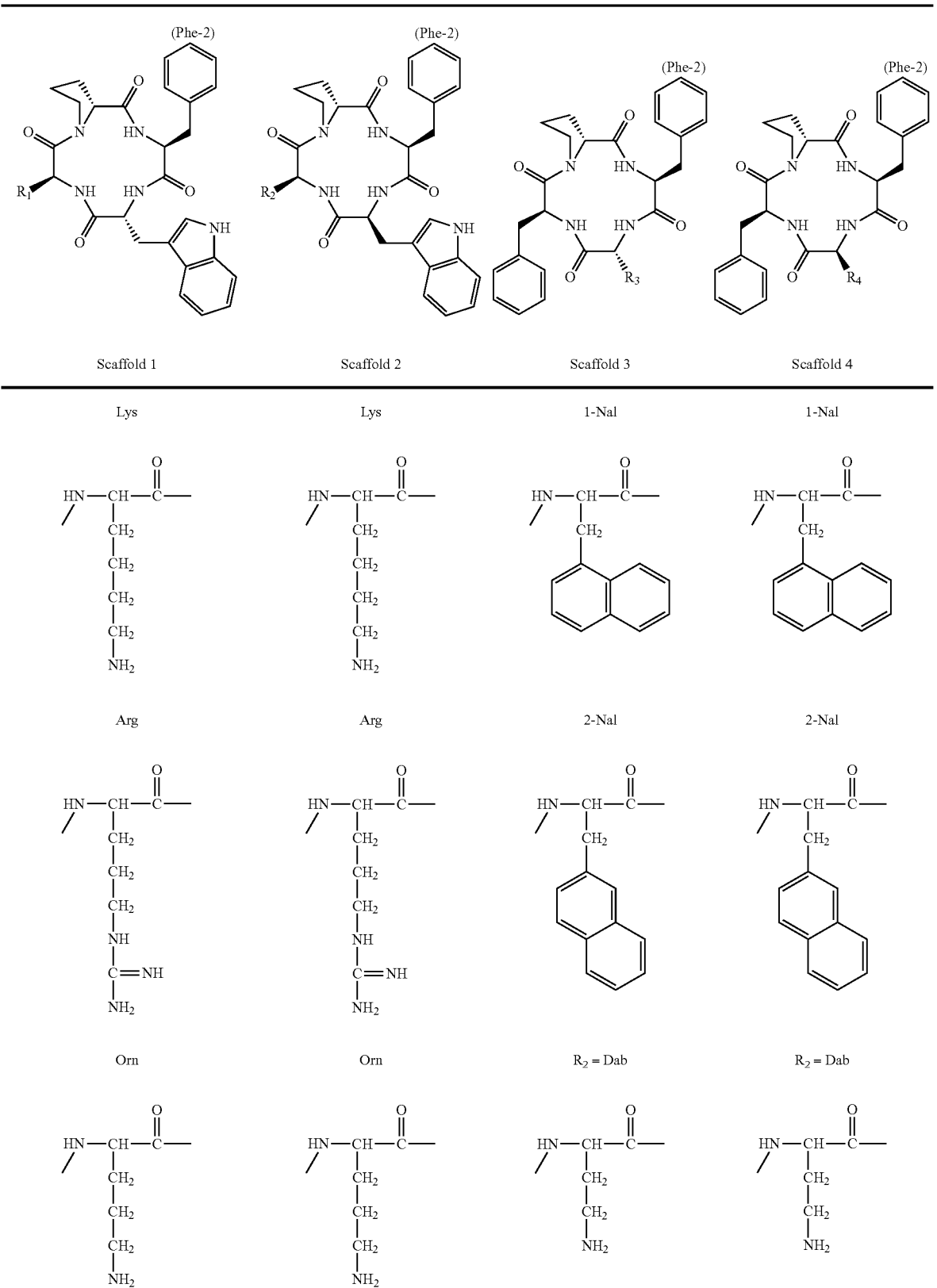
| Scaffold 1 | Scaffold 2 | Scaffold 3 | Scaffold 4 |
Lys / Lys / 1-Nal / 1-Nal
Arg / Arg / 2-Nal / 2-Nal
Orn / Orn / R₂ = Dab / R₂ = Dab TABLE 2-continued
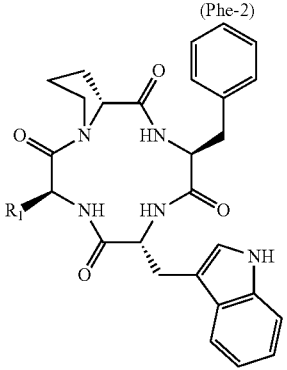

TABLE 2-continued
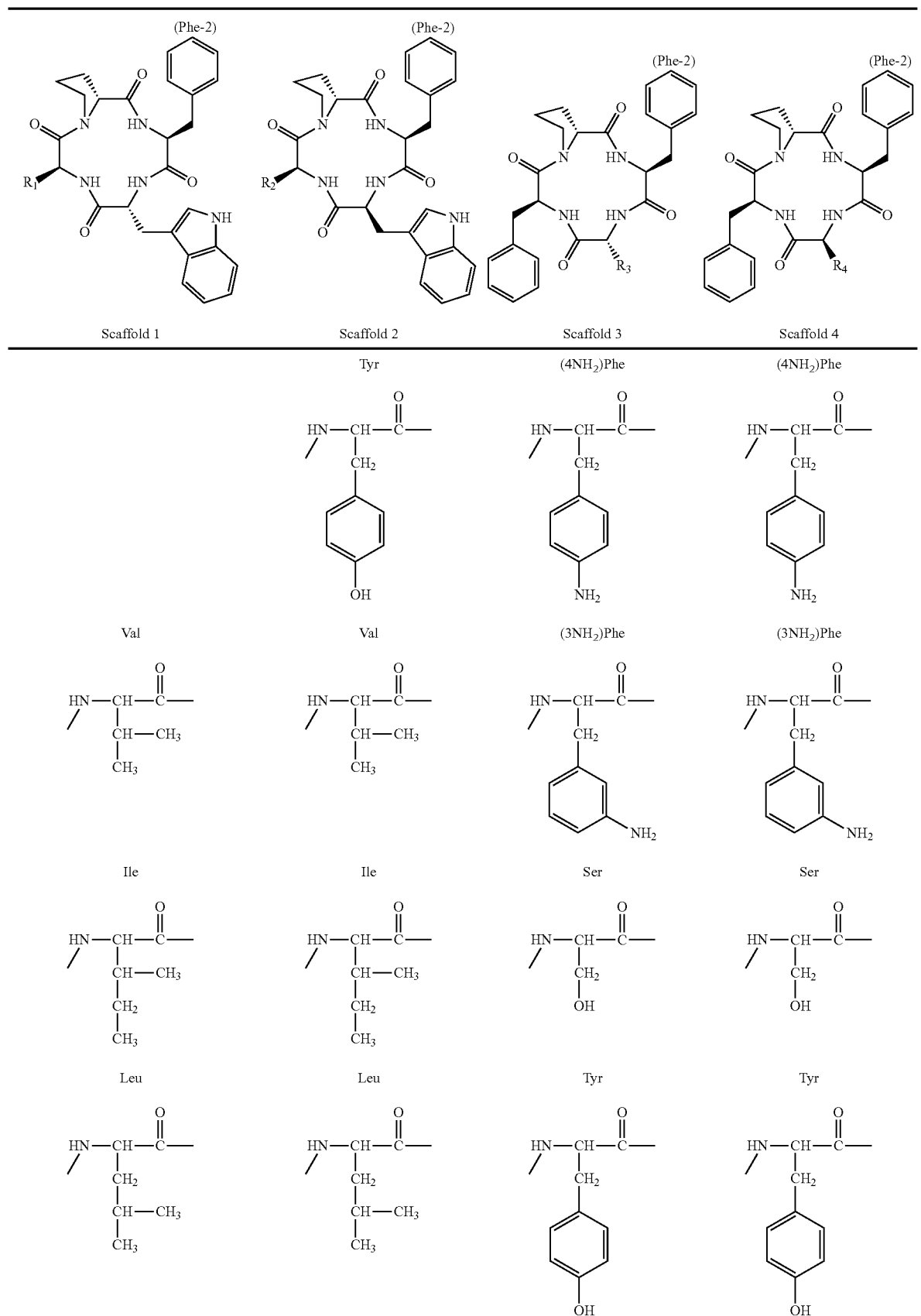

TABLE 2-continued

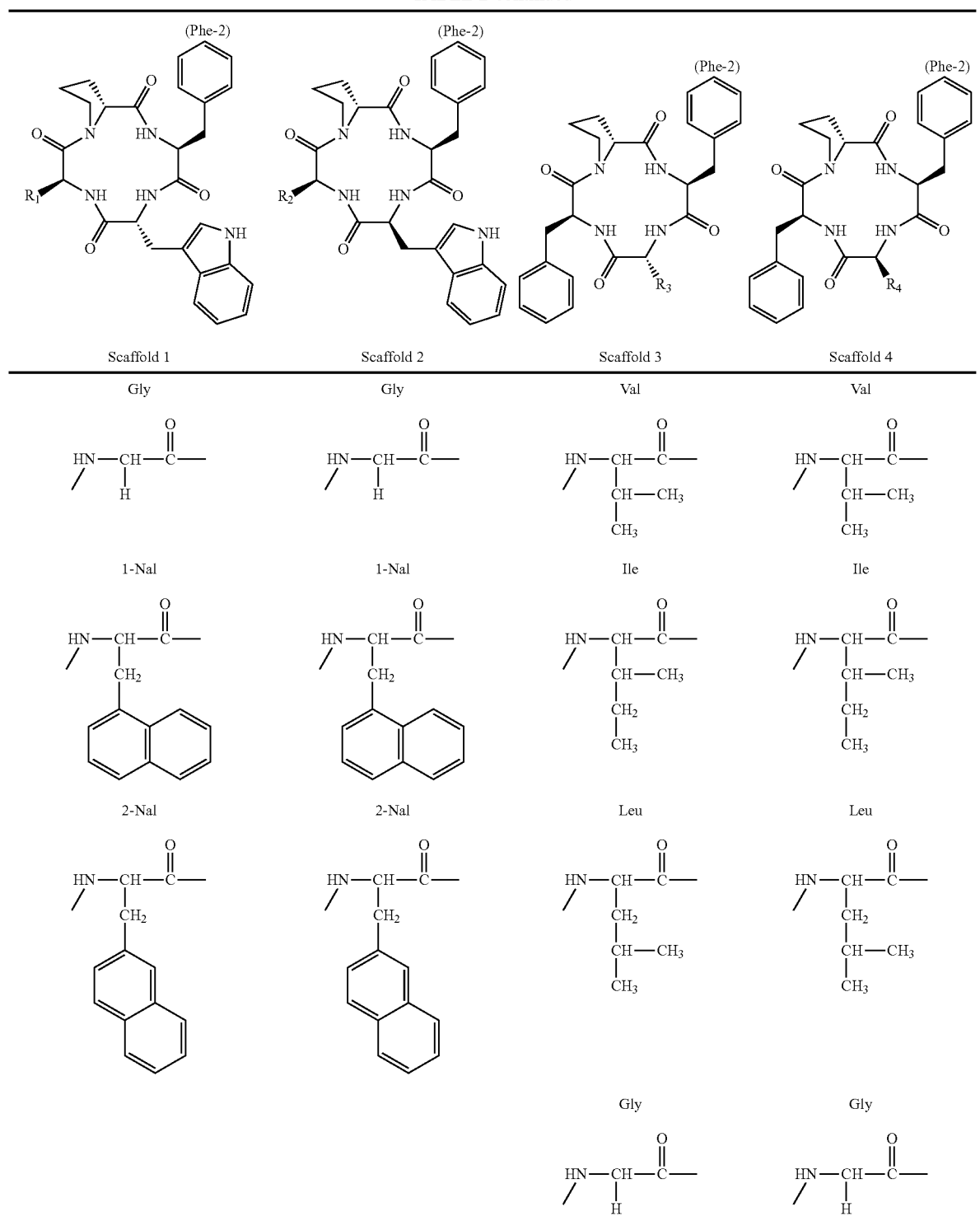

With regard to Scaffolds 1 and 2, the amino acid may not be Gly in certain embodiments. While the analogs of Scaffolds 1 and 2 may have lower in vitro action, these analogs may be beneficial in vivo.

In any of Scaffolds, 1-4, the Phe-2 residue can be substituted with any Phe analog, such as Tyr and mTyr, Tryp, 1-Nal, 2-Nal, cyclhexylalanine, Leu, aliphatic amino acids, and the like.

Synthesis of peptides, such as cyclic tetrapeptides and other polypeptides is well established. As such, with the disclosure of the amino acids of the cyclic tetrapeptides, a chemist can prepare the cyclic tetrapeptides of the present invention through routine experimentation.

The cyclic tetrapeptides can be administered to a subject via traditional routes of administration. Such routes include intravenous, intraperitoneal, subcutaneous, intrathecal, inhalation, nasal, transdermal, and the like. For example, subcutanteous (s.c.) administration of the cyclic tetrapeptides may result in an effective amount to cross the BBB so as to be active in the brain. This allows the cyclic tetrapeptides to block stress-induced reinstatement of cocaine-seeking behavior in animals. As such, the cyclic tetrapeptides can be included in a composition with a pharmaceutically acceptable carrier that is selected based on the mode of administration.

In one embodiment, the cyclic tetrapeptides can be encapsulated into a microsphere for oral administration. Alternatively, the cyclic tetrapeptides can be formulated so as to allow passage through and absorption from the gastrointestinal tract. Since the cyclic tetrapeptides are cyclic and more stable that linear polypeptides, they are expected to have better activity following oral administration.

However, there are other possible routes of administration that minimize or eliminate the need for regular injection of the compound. For example, depot formulations, such as temperature-reversable polymers or hydrogels, where the duration of action (e.g., from days to months) can be regulated by the formulation. Also, inhaled formulations and transdermal formulations can be prepared. The preparation of drug delivery formulations that include the proper adjuvants are well known for specific modes of delivery. Depot formulations for injection can be developed that control the duration of action (from a few days to months) minimizing the frequency of injection. Alternatively a formulation for inhalation (similar to the recently introduced inhaled insulin product) can be developed so that the drug does not have to be injected. Also, nasal administration can also be effective.

DEFINITIONS

As used herein, the terms "an effective amount", "therapeutic effective amount", or "therapeutically effective amount" shall mean an amount or concentration of a compound according to the present invention which is effective within the context of its administration or use. Thus, the term "effective amount" is used throughout the specification to describe concentrations or amounts of compounds according to the present invention which may be used to produce a favorable change in the disease or condition treated, inhibited, or prevented, whether that change is a remission, a decrease in desire for a drug such as cocaine or in addiction characteristics, a favorable physiological result, or the like, depending upon the disease or condition treated.

As used herein, the term "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient. The compositions of the present invention can include a pharmaceutically acceptable excipient.

As used herein, the term "pharmaceutically acceptable carrier" means a drug carrier that is useful in preparing a pharmaceutical composition that is generally safe, non-toxic and neither biologically nor otherwise undesirable, and includes a carrier that is acceptable for veterinary use as well as human pharmaceutical use. The compositions of the present invention can include a pharmaceutically acceptable carrier.

As used herein, the term "pharmaceutically acceptable salts" refers to those salts which retain the biological effectiveness and properties, which are not biologically or otherwise undesirable, and which are formed with inorganic acids such as hydrochloric acid, hydrobromic acid, sulfuric acid, nitric acid, phosphoric acid and the like, and organic acids such as trifluoroacetic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Groups which form pharmaceutically acceptable salts include amines, hydrazines, amidines, guanidines, substituted aryl/heteroaryl and substituted alkyl groups that carry at least a nitrogen bearing substitutent such as amino, guanidine, amidino, and the like.

As used herein, the term "coadministration" or "combination therapy" is used to describe a therapy in which at least two active compounds in effective amounts are used for the treatment, inhibition, and/or prevention of cocaine or other drug addiction, or cocaine or other drug-seeking activity, such as stress-induced drug-seeking activity. Although the term coadministration preferably includes the administration of two active compounds to the patient at the same time, it is not necessary that the compounds be administered to the patient at the same time, although effective amounts of the individual compounds will be present in the patient at the same time.

Compounds according to the present invention may be used in pharmaceutical compositions having biological/pharmacological activity for the treatment, inhibition, and/or prevention of cocaine or other drug addiction, or cocaine or other drug-seeking activity as described herein or for depression or anxiety. These compositions comprise an effective amount of any one or more of the compounds disclosed herein, optionally in combination with a pharmaceutically acceptable additive, carrier, or excipient.

As used herein, the term "treating" or "treatment" of a disease, including drug addiction and drug-seeking behavior, includes: (a) preventing the disease, i.e. causing the clinical symptoms of the disease not to develop in a mammal that may be exposed to or predisposed to the disease but does not yet experience or display symptoms of the disease; (b) inhibiting the disease, i.e., arresting or reducing the development of the disease or its clinical symptoms; or (c) relieving the disease, i.e., causing regression of the disease or its clinical symptoms.

As used herein, a "subject" or a "patient" refers to any mammal (preferably, a human), and preferably a mammal that may be susceptible to cocaine or other drug addiction, or cocaine or other drug-seeking activity. Examples of a subject or patient include a human, a non-human primate, a cow, a horse, a pig, a sheep, a goat, a dog, a cat or a rodent such as a mouse, a rat, a hamster, or a guinea pig. Generally, the invention is directed toward use with humans.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references, publications, journal articles, patents, published patent applications, and the like that are disclosed herein are incorporated herein by specific reference in their entirety.

EXPERIMENTAL

Opioid receptor affinities were determined for the cyclic tetrapeptides using Chinese hamster ovary cells stably expressing κ, μ and δ opioid receptors, and their efficacies at κ opioid receptors were determined in the adenylyl cyclase assay as previously described (Arttamangkul, et al., *J. Med. Chem.* 1997, 40, 1211-1218; Soderstrom, et al., *Eur. J. Pharmacol.* 1997, 338, 191-197). [$^3$H]Diprenorphine, [$^3$H][D-Ala$^2$,NMePhe$^4$,glyol]enkephalin and [$^3$H]cyclo[D-Pen$^2$,D-Pen$^5$]enkephalin were used as the radioligands in the binding assays for κ, μ and δ opioid receptors, respectively. In the adenylyl cyclase assay, the efficacies were determined by measuring the inhibition of adenylyl cyclase by 10 μM of the peptides relative to dynorphin A-(1-13) amide (100%). Table 1 shows the opioid receptor affinities and efficacy.

TABLE 1

| Compound | $K_i$ (nM ± SEM) | | | $K_i$ ratio | Cyclase screen[a] |
|---|---|---|---|---|---|
| | κ | μ | δ | (κ/μ/δ) | (% control) |
| L-Trp series | | | | | |
| c[Trp-Phe-D-Pro-Phe] (Compound 2801 or JVA-2801) | 35.4 ± 3.6 (4) | 619 ± 87 (3) | 4150 ± 3020 (3) | 1/17.5/117 | 119% |
| c[Trp-Ala-D-Pro-Phe] (Compound 2803 or JVA-2803) | 8.03 ± 1.67 (4) | 32.1 ± 3.9 (3) | 8680 ± 1270 (3) | 1/4.0/1080 | 122% |
| D-Trp series: | | | | | |
| c[D-Trp-Phe-D-Pro-Phe] (Compound 2802 or JVA-2802) | 30.6 ± 3.4 (5) | 259 ± 29 (3) | 2910 ± 1350 (3) | 1/8.5/95 | 127% |
| c[D-Trp-Ala-D-Pro-Phe] (Compound 3003 or JVA-3003) | 3.15 ± 0.41 (3) | 27.3 ± 2.7 (3) | 8330 ± 1220 (3) | 1/8.7/2640 | 75% |

[a]Relative to dynorphin A-(1-13) amide (100%)

An antinociceptive (analgesic) assay was performed to test the KOR agonist activity of cyclic tetrapeptides cyclo[Trp-Phe-D-Pro-Phe] (Compound 2801 or JVA-2801), cyclo[Trp-Ala-D-Pro-Phe] (Compound 2803 or JVA-2803), JVA-3003, and JVA-2802 by using a 55° C. warm-water tail-withdrawal assay in C57B1/6J mice. Briefly, warm (55° C.) water was used as the thermal nociceptive stimulus, with the latency of the mouse to withdraw its tail from the water taken as the endpoint (McLaughlin, J. P.; Hill, K. P.; Jiang, Q.; Sebastian, A.; Archer, S.; Bidlack, J. M. Nitrocinnamoyl and chlorocinnamoyl derivatives of dihydrocodeinone: in vivo and in vitro characterization of mu-selective agonist and antagonist activity. *J. Pharmacol. Exp. Ther.* 1999, 289, 304-311.). After determining baseline tail-withdrawal latencies, mice received a single intracerebroventricular (i.c.v.) dose of vehicle (artificial cerebrospinal fluid, 146 mM NaCl, 2.7 mM KCl, 1.2 mM, $CaCl_2$, 1.0 mM $MgCl_2$) or a dose of test compound i.c.v. and the tail-withdrawal latency was again measured. The time that a compound was administered relative to determining tail-withdrawal latency is indicated in the figure legends. For i.c.v. injections, each mouse was lightly anesthetized with isoflurane, an incision was made in the scalp, and the injection was made 2 mm lateral and 2 mm caudal to bregma at a depth of 3 mm directly into the lateral ventricle, as detailed previously (McLaughlin et al., 1999). The volume of these injections was 5 μl, using a 10-μl Hamilton microliter syringe. Reference agonists and antagonists were administered either subcutaneously (s.c.) or interperitoneally (i.p.) in 0.9% saline at the doses and times indicated in the figure legends (negative numbers indicate time prior to tail-withdrawal assay).

Figure 1B:
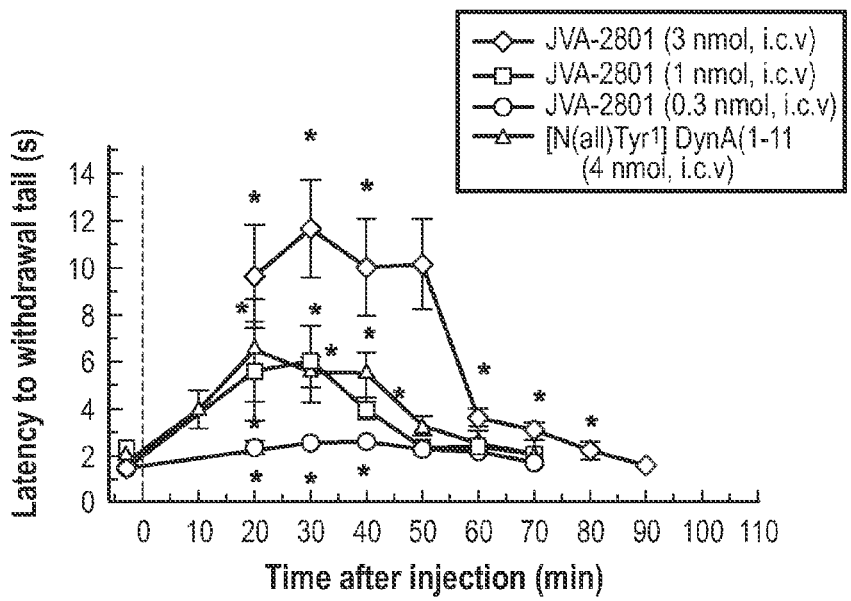

FIGS. 1A-1B show the results of the KOR agonist activity of cyclic tetrapeptides cyclo[Trp-Phe-D-Pro-Phe] (Compound 2801 or JVA-2801), cyclo[Trp-Ala-D-Pro-Phe](Compound 2803 or JVA-2803). The data show surprising and unexpected results in that the cyclic tetrapeptides JVA-2801 and JVA-2803 can function as agonists. The opioid receptor involvement in the agonist activity of JVA-2801 was assessed by treatment with the mu opioid receptor (MOR) selective antagonist beta-FNA, KOR selective antagonist norBNI, and the delta opioid receptor selective (DOR) antagonist naltrindole.

Figure 1C:
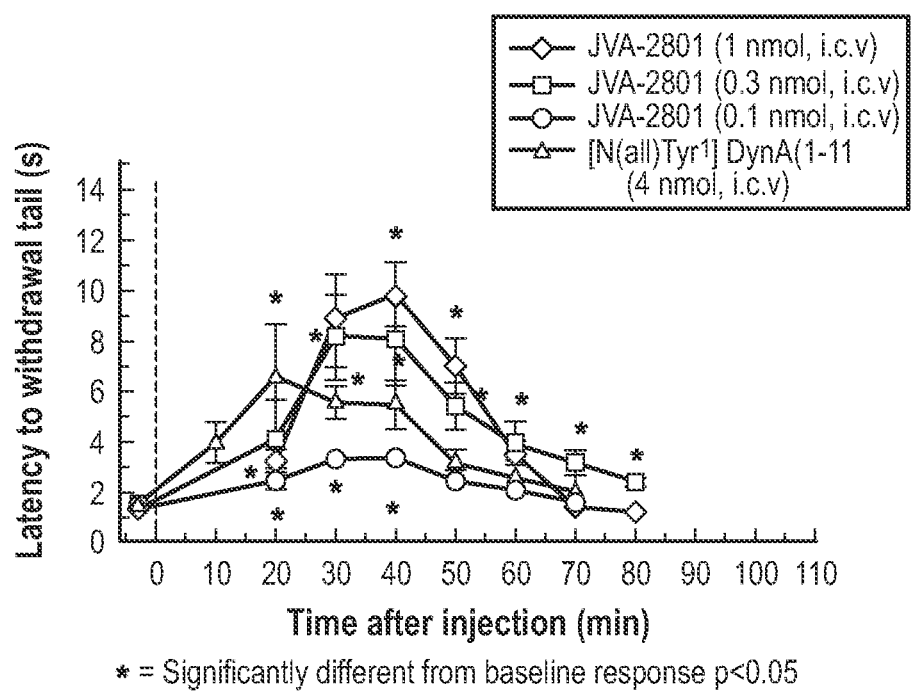

FIG. 1C shows the agonist activity of JVA-3003 in the 55° C. warm water tail withdrawal assay following i.c.v. administration. However, JVA-2802 did not show any agonist activity. The data show surprising and unexpected results in that the cyclic tetrapeptide JVA-3003 can function as an agonist.

In view of the foregoing, the agonist activity of selected cyclic tetrapeptides was surprising and unexpected, given the original report (Saito et al., *J. Antibiot.* 2002, 55, 847-854) that the natural product CJ-15,208 was a KOR antagonist.

Figure 2:
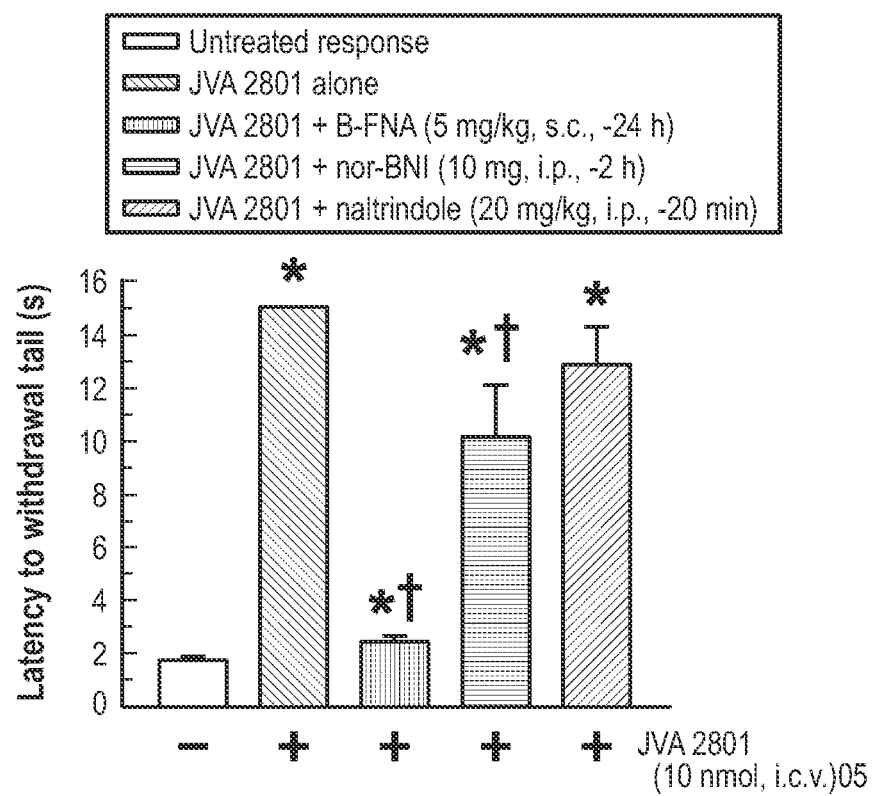
FIG. 2 illustrates opioid receptor involvement in the agonist activity of JVA-2801, as assessed by treatment with the mu opioid receptor (MOR) selective antagonist beta-FNA, KOR selective antagonist norBNI, and the delta opioid receptor selective (DOR) antagonist naltrindole.

FIG. 2 shows the opioid receptor involvement in the agonist activity of JVA-2801, as assessed by treatment with the mu opioid receptor (MOR) selective antagonist beta-FNA, KOR selective antagonist norBNI, and the delta opioid receptor selective (DOR) antagonist naltrindole.

Figure 3A:
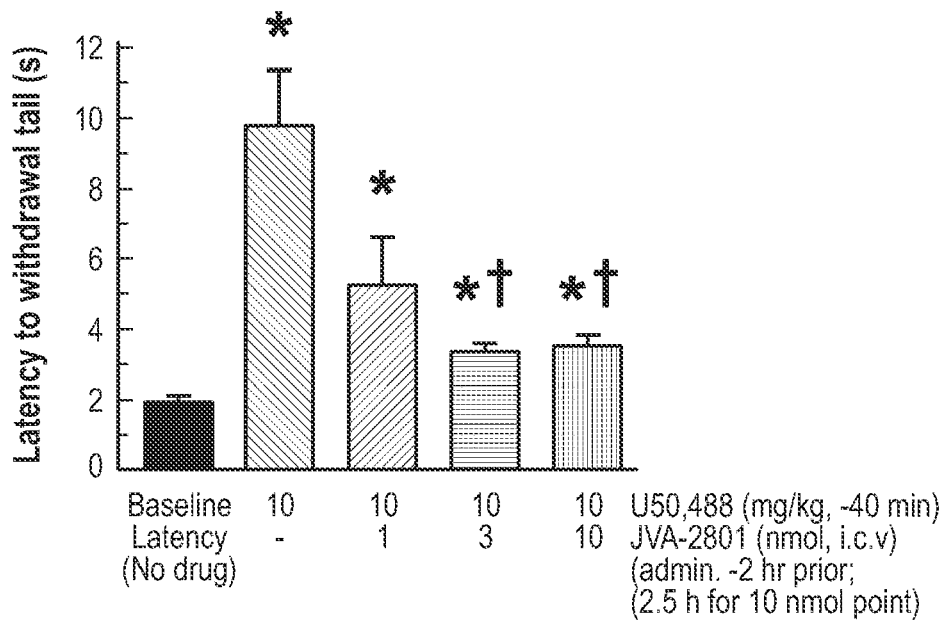
FIGS. 3A-3D illustrate the ability of cyclic tetrapeptides to antagonize the KOR selective agonist U50,488 (tested 2-2.5 hours after peptide administration), where
Figure 3B:
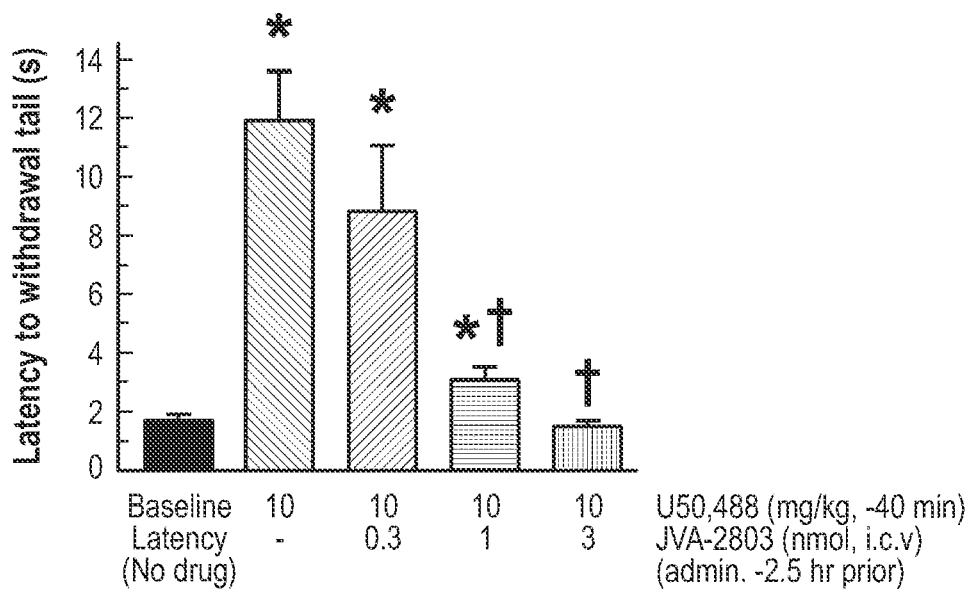
Figure 3C:
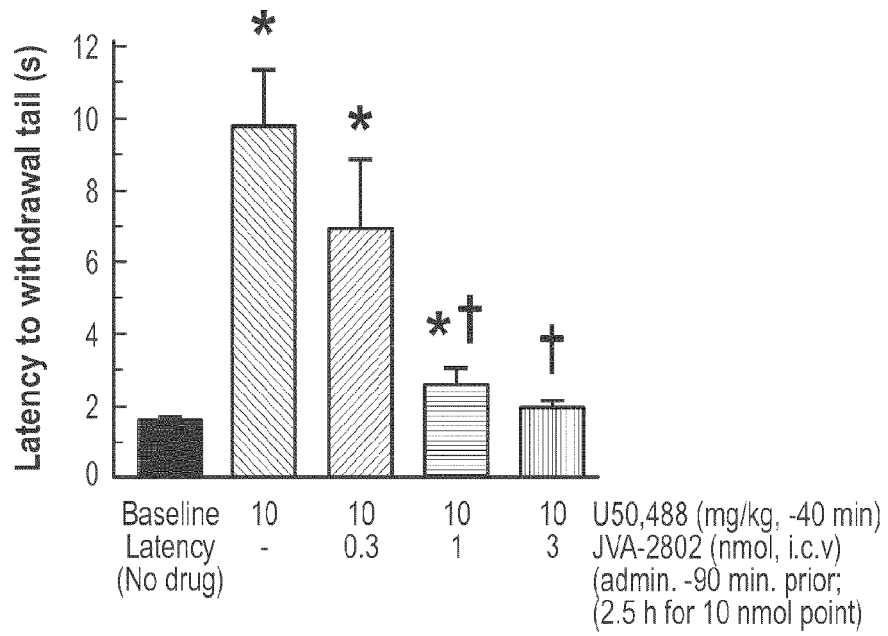
Figure 3D:
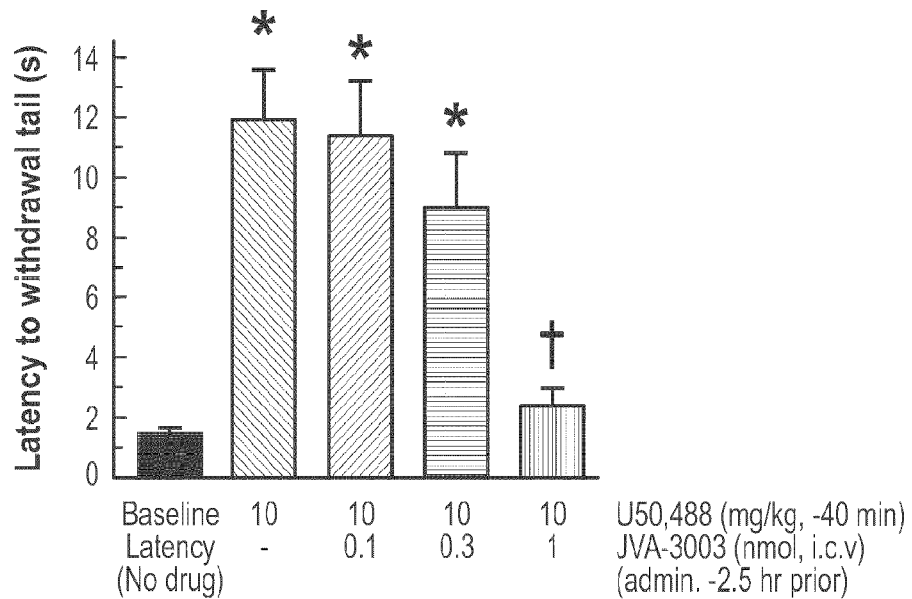

The ability of the cyclic tetrapeptides to function as KOR antagonists were studied by assessing the ability to antagonize the KOR selective agonist U50,488. FIGS. 3A-3D show the ability of the cyclic tetrapeptides (FIG. 3A JVA-2801; FIG. 3B JVA-2803; FIG. 3C JVA-2802; FIG. 3D JVA-3003) to antagonize the KOR selective agonist U50,488. Briefly, the antagonistic activity was tested 2-2.5 hours after peptide administration.

Figure 4A:
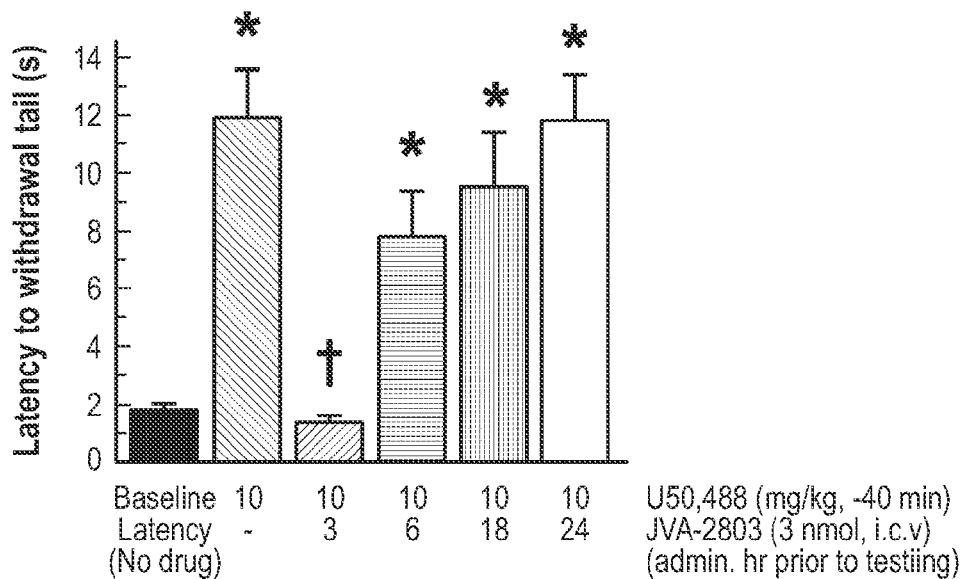
FIG. 4A-4C show the duration of KOR antagonism of cyclic tetrapeptides.
Figure 4B:
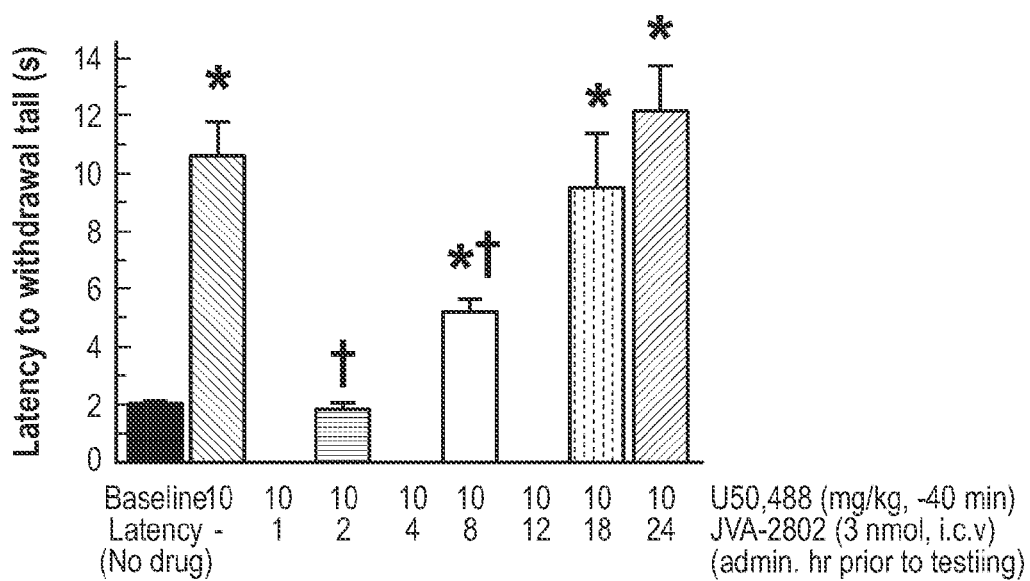
Figure 4C:
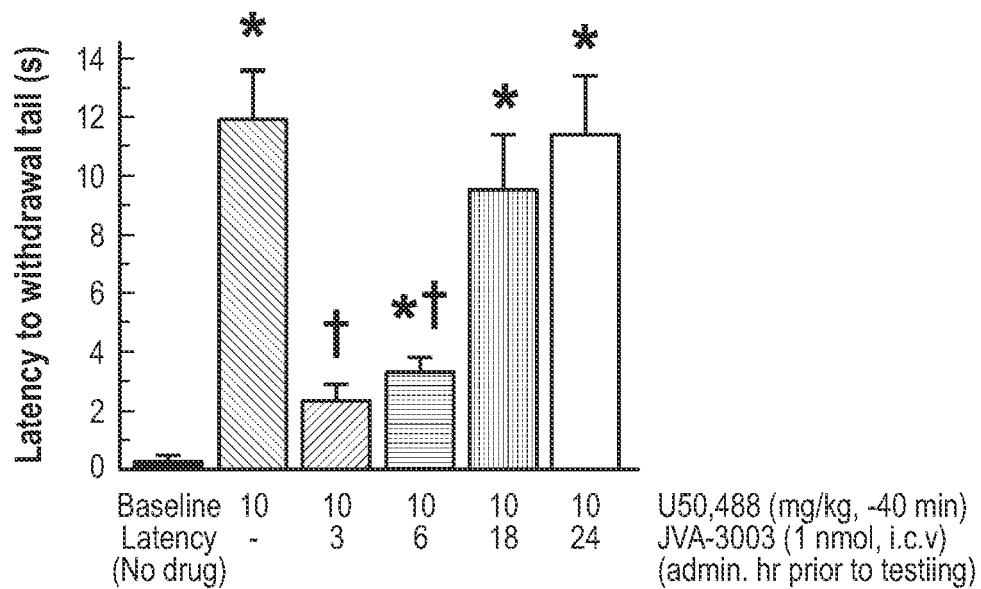

The duration of KOR antagonism of the cyclic tetrapeptides was studied. FIG. 4A shows the duration of KOR antagonism of JVA-2803. FIG. 4B shows the duration of KOR antagonism of JVA-2802. FIG. 4C shows the duration of KOR antagonism by JVA-3003. The data show surprising and unexpected results in that the relatively short duration of the antagonist activity of the cyclic tetrapeptides (FIGS. 4 and 7) is very significant. All of the small molecule KOR selective antagonists reported to date exhibit exceptionally long activity (lasting weeks to more than a month after a single dose). This unexplained prolonged activity would be a concern to the FDA and could prevent or severely limit the use of these compounds in patients. The antagonist activity of the cyclic tetrapeptides lasts less than a day, so that these compounds do not raise the concerns of the small molecule antagonists. To date there has been only one other selective KOR antagonist, the structurally unrelated peptide antagonist zyklophin identified in our laboratory, with KOR antagonist activity that lasts less than a day.

The ability of JVA-2802 to selectively antagonize an opioid receptor was studied. Briefly, the antagonistic activity of JVA-2802 was studied for MOR, DOR, and KOR activity by the ability to antagonize the MOR selective agonist morphine, the DOR selective agonist SNC-80, and the KOR selective agonist U50,488.

Figure 5:
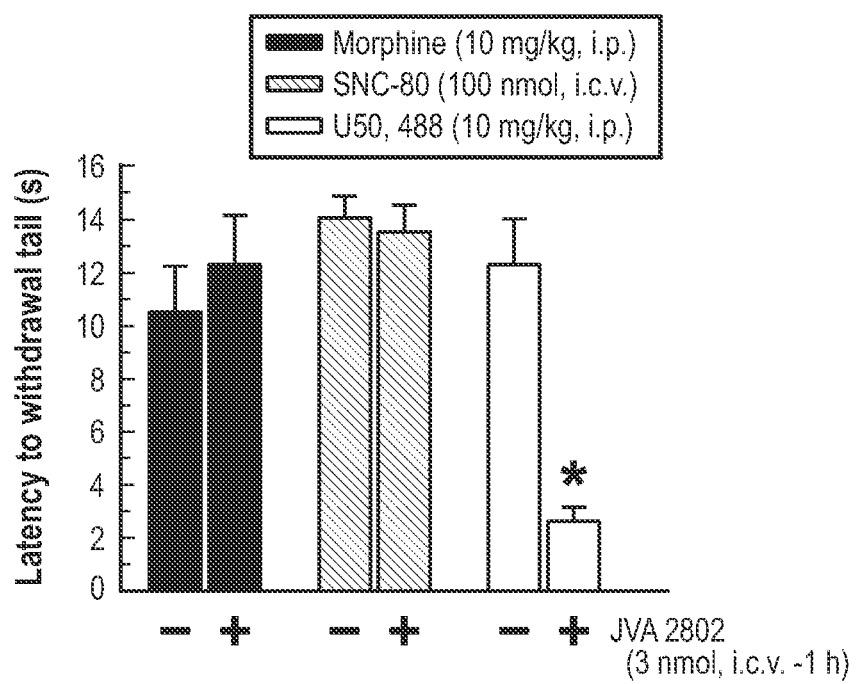
FIG. 5 illustrates opioid receptor selectivity of JVA-2802, as measured by its ability to antagonize the MOR selective agonist morphine, the DOR selective agonist SNC-80, and the KOR selective agonist U50,488.

FIG. 5 shows the opioid receptor selectivity of JVA-2802, as measured by its ability to antagonize the MOR selective agonist morphine, the DOR selective agonist SNC-80 and the KOR selective agonist U50,488. JVA-2802 is selective for KOR, and does not antagonize the MOR selective agonist morphine or the DOR selective agonist SNC-80.

In view of the foregoing, assays have evaluated four cyclic tetrapeptides, cyclo[Trp-Phe-D-Pro-Phe] (JVA-2801), which appears to be the natural product CJ-15,208, and its alanine analog cyclo[Trp-Ala-D-Pro-Phe] (JVA-2803), and the corresponding D-Trp analogs cyclo[D-Trp-Phe-D-Pro-Phe] (JVA-2802) and cyclo[D-Trp-Ala-D-Pro-Phe] (JVA-3003) in vivo in an analgesic assay, the 55° C. warm water tail withdrawal assay (FIGS. 1-5).

Based on the opioid receptor affinities determined in vitro (Table 1) and the reported kappa opioid receptor (KOR) antagonist activity of the natural product in the rabbit vas deferens, it was expected JVA-2801 to exhibit antagonist activity in vivo. As such, it was surprising and unexpected when JVA-2801 exhibited robust agonist activity following intracerebroventricular (i.c.v.) administration (FIG. 1A). The mu opioid receptor (MOR) selective antagonist β-FNA completely reversed the agonist activity of JVA-2801, indicating MOR involvement in the observed agonism. This was very surprising, given the low MOR receptor affinity of JVA-2801. The KOR selective antagonist nor-BNI partially reversed the agonist activity of JVA-2801, suggesting that the peptide also exhibited agonist activity at KOR. When tested 2-2.5 hours after its administration, when the agonist activity had dissipated (FIG. 1A), the peptide exhibited dose-dependent antagonism of the KOR selective agonist U50,488 (FIG. 3A).

Also, JVA-2803, an alanine analog of JVA-2801, was surprisingly shown to exhibit 4-fold higher KOR affinity and 19-fold higher MOR affinity in radioligand binding assays (Table 1). The pattern of activity of JVA-2803 in vivo is similar to that of JVA-2801. This is consistent with the binding affinities of JVA-2803 being more potent than JVA-2801, both as an agonist and as an antagonist. The duration of the antagonist activity of JVA-2803 is shown in FIG. 4A. In contrast to the nonpeptide KOR selective antagonists, which exhibit exceptionally long activity (lasting weeks to more than a month after a single dose), the duration of the antagonist activity of the cyclic tetrapeptide JVA-2803 is less than a day (FIG. 4A).

Figure 6:
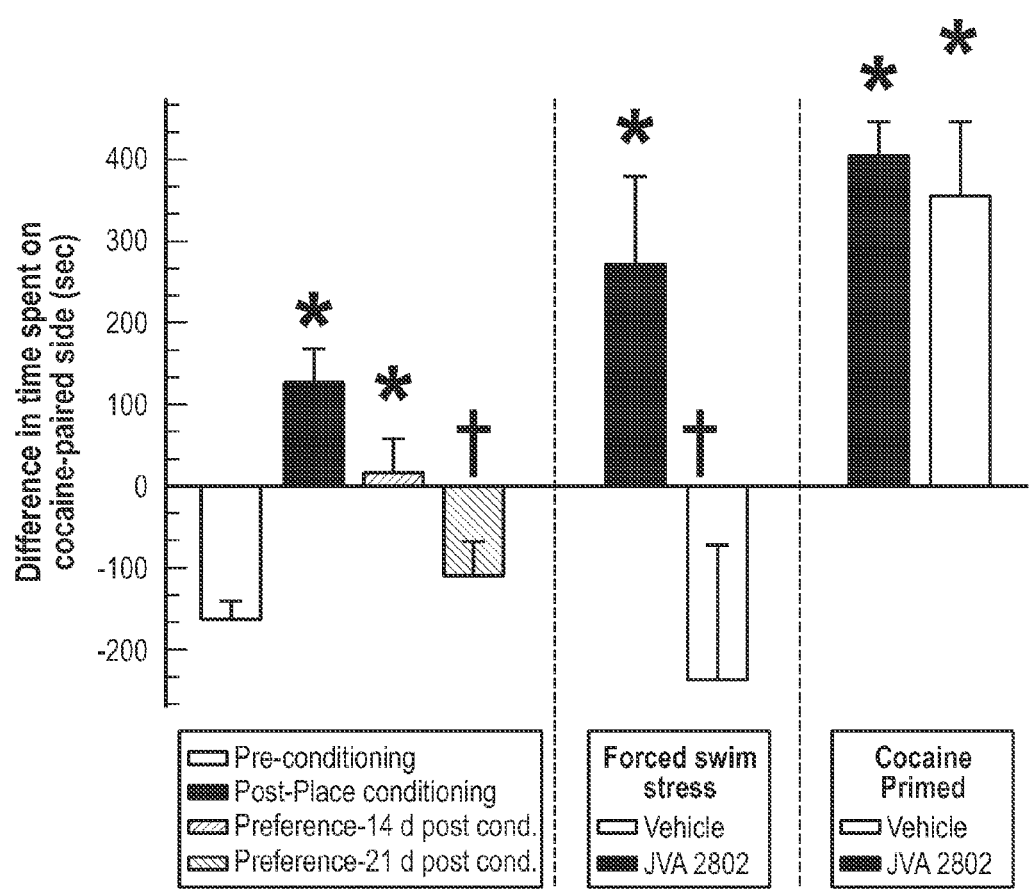
FIG. 6 illustrates the ability of JVA-2802 to block stress-induced reinstatement of cocaine conditioned place preference.

In contrast to the L-Trp peptide, the D-Trp cyclic tetrapeptide JVA-2802 did not exhibit any agonist activity in vivo, and showed only antagonist activity. Treatment with JVA-2802 caused dose-dependent antagonism of U50,488 (FIG. 3C) which lasted less than a day (FIG. 4B). JVA-2802 is selective for KOR, and does not antagonize the MOR selective agonist morphine or the DOR selective agonist SNC-80 (FIG. 5). As discussed later, this peptide also blocks stress-induced reinstatement of cocaine conditioned place preference (FIG. 6).

In contrast to JVA-2802, the alanine analog JVA-3003 exhibits robust agonist activity (FIG. 1C). Similar to JVA-2801 and 2803, JVA-3003 exhibits KOR antagonist activity (FIG. 3D) when tested 2.5 hours after its administration, when its agonist activity has dissipated. Similar to JVA-2802 and 2803 the duration of the KOR antagonist activity lasts less than a day (FIG. 4C).

In summary, these cyclic tetrapeptides exhibit an unusual pattern of opioid activity in vivo. The L-Trp parent peptide, JVA-2801, which may be the natural product CJ-15,208, along with its alanine analog JVA-2803, exhibit both agonist activity and KOR antagonist activity. This pattern of activity could be beneficial, since evidence suggests that KOR antagonist activity can improve the side effect profile of MOR analgesics. Thus KOR deficient mice exhibit attenuated morphine withdrawal and treatment with the KOR selective antagonist JDTic decreases morphine withdrawal symptoms. In the D-Trp series, the parent peptide JVA-2802 does not exhibit any agonist activity but only antagonist activity, while the alanine analog JVA-3003 exhibits a pattern similar to the L-Trp peptides. JVA-2802 is a selective KOR antagonist in vivo with antagonist that lasts less than a day; this duration of activity is in stark contrast to the effects seen with the nonpeptide KOR selective antagonists, and thus could offer significant advantages for use as a pharmacological tool and potentially as a therapeutic agent.

Also, some of the cyclic tetrapeptides (i.e., cyclo[Trp-Ala-D-Pro-Phe] and cyclo[D-Trp-Ala-D-Pro-Phe]) exhibit an unusual and unexpected pattern of opioid activity in vivo, namely agonist activity plus KOR antagonist activity. This pattern of activity could be beneficial, since evidence suggests that KOR antagonist activity can improve the side effect profile of mu opioid receptor analgesics (e.g., attenuate morphine withdrawal symptoms).

Moreover, the substantial increases in KOR affinity of the alanine-substituted analogs cyclo[Trp-Ala-D-Pro-Phe] and cyclo[D-Trp-Ala-D-Pro-Phe] compared to the parent peptides was surprising and unexpected. Generally, substitution of alanine for other amino acids in a peptide leads to either a large decrease or no change in affinity for the target.

Assays to study the effects of cyclic tetrapeptides as KOR antagonists were conducted with cocaine conditioned place preference, extinction and stress-induced reinstatement (see FIG. 6). The establishment of cocaine conditioned place preference (CPP), extinction and stress-induced reinstatement of cocaine CPP were preformed in C57B1/6J mice as previously described (Carey, A. N.; Borozny, K.; Aldrich, J. V.; McLaughlin, J. P. Reinstatement of cocaine place-conditioning prevented by the peptide kappa-opioid receptor antagonist arodyn. *Eur. J. Pharmacol.* 2007, 569, 84-89). Briefly, mice were allowed to freely explore the apparatus for 30 min, demonstrating individual baseline place preferences. Place conditioning subsequently began immediately following cocaine administration (10 mg/kg s.c), whereupon mice were consistently confined for 30 min in the appropriate compartment in the CPP apparatus. Conditioning with assay vehicle (0.9% saline) followed 4 hours later in a similar manner, but paired to the opposite chamber. This conditioning cycle was repeated once on each of four days. On the fifth day, mice were again allowed to freely move through the apparatus. Post-conditioning place preference for the cocaine-paired compartment was judged successful when mice demonstrated a significant increase in the difference in time spent in the cocaine-paired chamber over the initial preferences. Place preference for the cocaine-paired compartment was then re-examined weekly to confirm extinction, defined as a statistically significant decrease in the time spent in the cocaine-paired compartment during the extinction trial as compared to the immediate post-conditioning response. Conditioned place preference responses subsided with repeated testing over a 3-week period (FIG. 6, left panel).

Mice demonstrating extinction of cocaine-conditioned place preference were then divided into groups. One group of animals was then subjected to a 2-day forced swim stress protocol (with a single long swim (15 minutes) on day 1, and a series of four 6-minutes trials on day 2) to produce reinstatement of cocaine CPP. Mice were pretreated each day with vehicle or JVA-2802 (3 nmol i.c.v.) 40 minutes prior to exposure to forced swim stress. One hour after the final exposure to forced swim stress, the place preference responses of the mice were determined as described above to determine possible reinstatement of cocaine CPP (FIG. 6, middle panel). A second group of mice were pretreated with vehicle or JVA-2802 prior to one additional cycle of cocaine place conditioning as described above, and animals were tested for place preference one hour later (FIG. 6, right panel). Data are plotted as the difference in time spent in the eventual cocaine- and vehicle paired compartments, such that by convention a positive value reflects a conditioned preference for the cocaine-paired side.

Additional Findings

It was found that Formula 1 has an affinity for KOR in mouse brain with Ki being about 21 nM, and the affinity for Formula 2 is Ki being 47 nM.

While not shown, an overlay of Formula 1 and Formula 2 shows that the Phe(1) and Phe(2) residues in the two peptides each occupy similar space in binding KOR.

Evidence was obtained to illustrate that two aromatic residues, such as those shown in the cyclic tetrapeptides herein, may be important for KOR affinity.

The KOR, MOR, and DOR for select cyclic tetrapeptides were as follows: JVA 3001 having KOR Ki being 68.9 nM, MOR Ki being 58.1 nM, and DOR Ki being 5690 nM; JVA 3002 having KOR Ki being 1250 nM, MOR Ki being 774 nM, and DOR Ki being 11000 nM; JVA 3003 having KOR Ki being 2.81 nM, MOR Ki being 27.3 nM, and DOR Ki being 833 nM; and JVA 3004 having KOR Ki being 169 nM, MOR Ki being 186 nM, and DOR Ki being 18000 nM. Data for other cyclic tetrapeptides (e.g., ala scan derivatives), such as compounds JVA-2803, 2804, 2805, and 2806, are shown in FIG. 7. The study was done using [$^3$H]diprenorphine, [$^3$][D-Ala$^2$,NMePhe$^4$,glyol]enkephalin and [$^3$H]cyclo[D-Pen$^2$,D-Pen$^5$]enkephalin binding to CHO membranes expressing KOR, MOR and DOR, respectively.

FIG. 7 provides a table with a summary of the affinity data for various cyclic tetrapeptides for KOR, MOR, and DOR.

Antagonists for kappa opioid receptors (KOR) have potential therapeutic applications in the treatment of drug abuse. The use of selective nonpeptide KOR antagonists in vivo, however, is often complicated by unusually long activity. Peptide KOR antagonists can exhibit shorter duration of action (hours) due to metabolism by proteases, and sought to identify systemically active peptide KOR antagonists that are metabolically stable and can cross the blood-brain barrier (BBB). Presently, the novel peptide zyklophin (PCT/US2008/079614) permeated the BBB in the BBMEC model, and exhibits a dose-dependent KOR-, but not MOR- or DOR-, selective antagonism in the 55° C. warm-water tail-withdrawal assay in mice following either systemic (s.c.) or central (i.c.v.) administration that lasted up to 18 h. Interestingly, s.c. administration of this peptide also blocks stress-induced reinstatement of cocaine conditioned place preference.

The invention claimed is:

1. A cyclic tetrapeptide, wherein the cyclic tetrapeptide comprises a structure of Scaffold 1 or a derivative thereof:

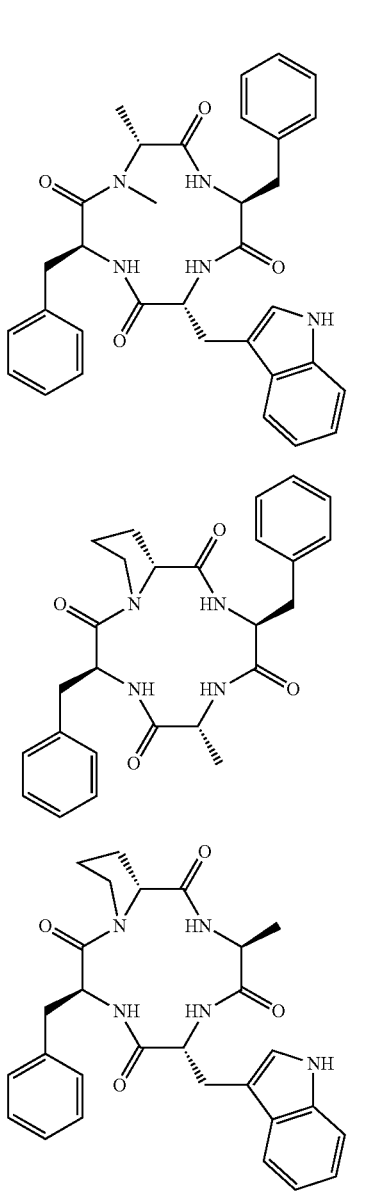

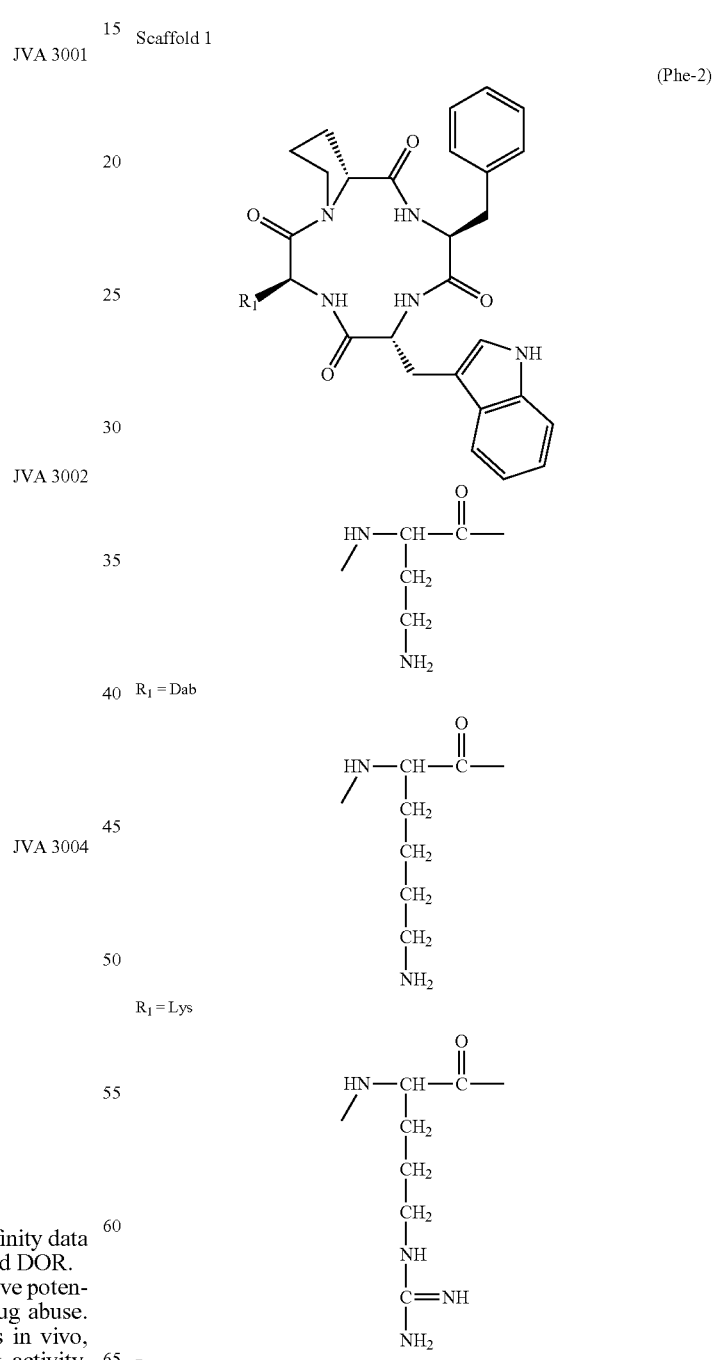

-continued

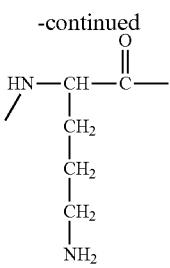
R₁ = Orn

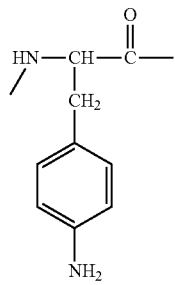
R₁ = (4NH₂)Phe

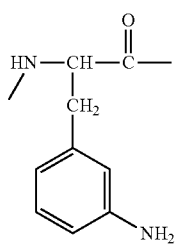
R₁ = (3NH₂)Phe

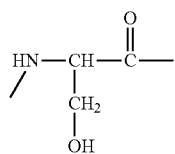
R₁ = Ser

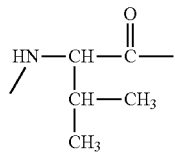
R₁ = Val

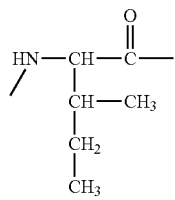
R₁ = Ile

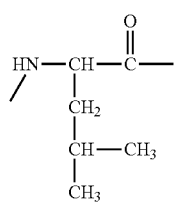

-continued

R₁ = Leu

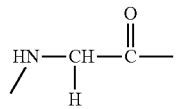
R₁ = Gly wherein the

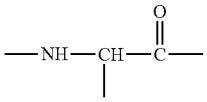

portion of the Dab, Lys, Arg, Orn, (4NH₂)Phe, (3NH₂)Phe, Ser, Val, Ile, Leu, and Gly structures is of Scaffold 1.

2. A cyclic tetrapeptide as in claim 1, wherein the Phe-2 residue is substituted with any Phe analog.

3. A cyclic tetrapeptide as in claim 2, wherein the Phe analog is one of Tyr, mTyr, Tryp, 1-Nal, 2-Nal, cyclhexylalanine, Leu, aliphatic amino acids, and derivatives thereof.

4. A cyclic tetrapeptide, wherein the cyclic tetrapeptide comprises a structure of Scaffold 2 or a derivative thereof:

Scaffold 2

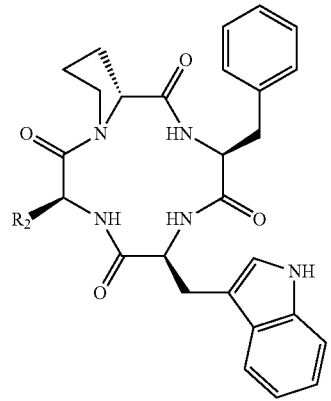
(Phe-2)

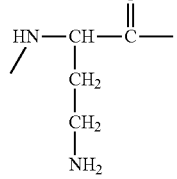
R₂ = Dab

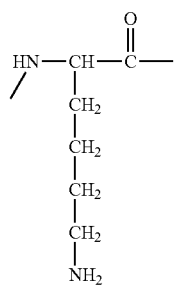

R₂ = Lys
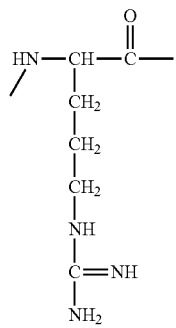
R₂ = Arg
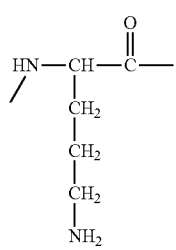
R₂ = Orn
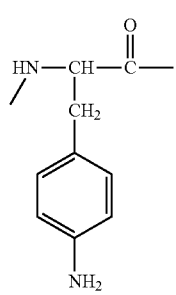
R₂ = (4NH₂)Phe
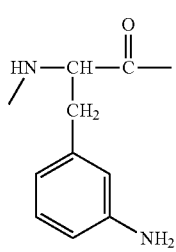
R₂ = (3NH₂)Phe
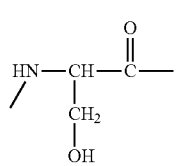
R₂ = Ser
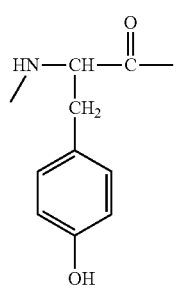
R₂ = Tyr
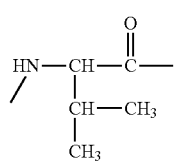
R₂ = Val
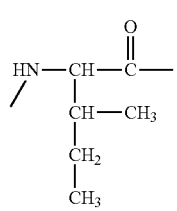
R₂ = Ile
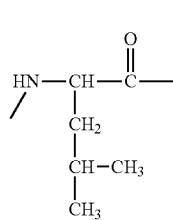
R₂ = Leu
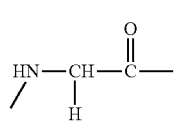
R₂ = Gly
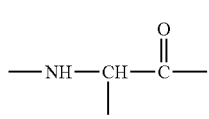
wherein the
portion of the Dab, Lys, Arg, Orn, (4NH₂)Phe, (3NH₂)Phe, Ser, Tyr, Val, Ile, Leu, and Gly structures is of Scaffold 2.

5. A cyclic tetrapeptide, wherein the cyclic tetrapeptide comprises a structure of Scaffold 3 or a derivative thereof:
Scaffold 3
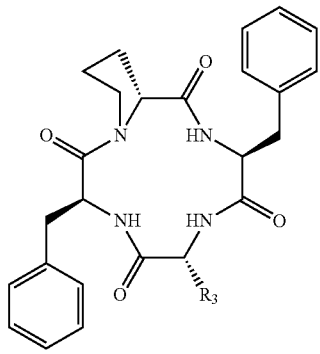
(Phe-2)
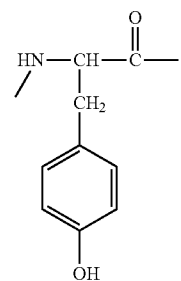
$R_3$ = Tyr
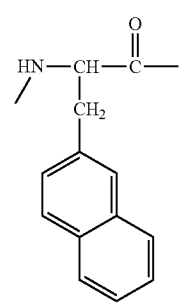
$R_3$ = 1-Nal
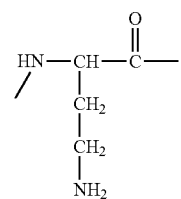
$R_3$ = 2-Nal
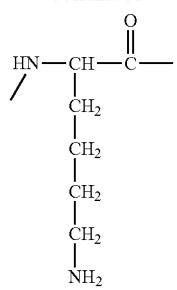
$R_3$ = Dab
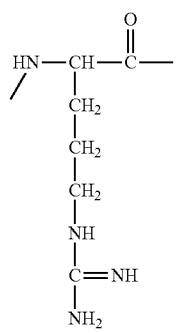
$R_3$ = Lys
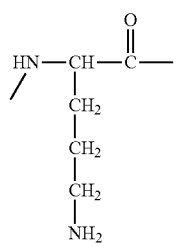
$R_3$ = Arg
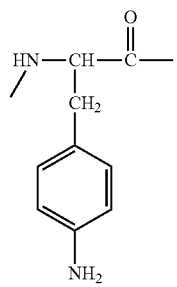
$R_3$ = Orn
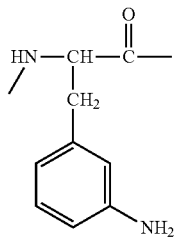
$R_3$ = (4NH$_2$)Phe -continued R₃ = (3NH₂)Phe

[structure: HN—CH(CH₂OH)—C(=O)—]

R₃ = Ser

[structure: HN—CH(CH(CH₃)₂)—C(=O)—]

R₃ = Val

[structure: HN—CH(CH(CH₃)CH₂CH₃)—C(=O)—]

R₃ = Ile

[structure: HN—CH(CH₂CH(CH₃)₂)—C(=O)—]

R₃ = Leu

[structure: HN—CH₂—C(=O)—]

R₃ = Gly wherein the

[structure: —NH—CH(R)—C(=O)—]

portion of the Tyr, 1-Nal, 2-Nal, Dab, Lys, Arg, Orn, (4NH₂) Phe, (3NH₂)Phe, Ser, Val, Ile, Leu, and Gly structures is of Scaffold 3.

6. A cyclic tetrapeptide, wherein the cyclic tetrapeptide comprises a structure of Scaffold 4 or a derivative thereof:

Scaffold 4

(Phe-2)

[cyclic tetrapeptide structure with R₄]

[structure: HN—CH(CH₂-C₆H₄-OH)—C(=O)—]

R₄ = Tyr

[structure: HN—CH(CH₂-1-naphthyl)—C(=O)—]

R₄ = 1-Nal

[structure: HN—CH(CH₂-2-naphthyl)—C(=O)—]

R₄ = 2-Nal

[structure: HN—CH(CH₂CH₂NH₂)—C(=O)—]

R₄ = R₂ = Dab

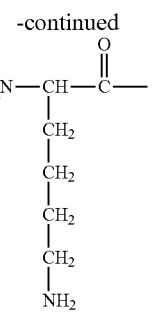

$R_4$ = Lys

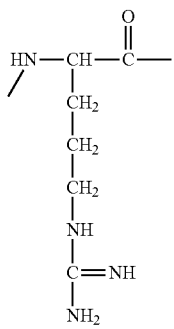

$R_4$ = Arg

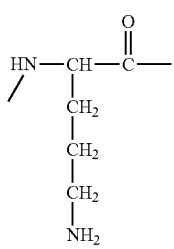

$R_4$ = Orn

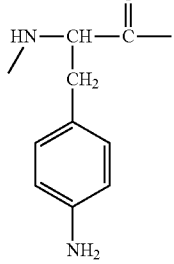

$R_4$ = (4NH$_2$)Phe

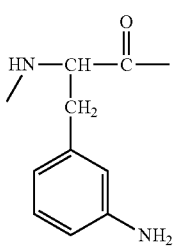

$R_4$ = (3NH$_2$)Phe

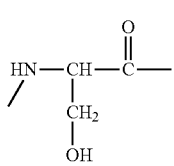

$R_4$ = Ser

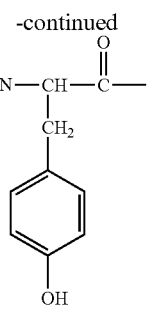

$R_4$ = Tyr

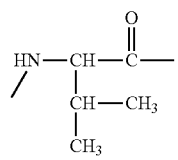

$R_4$ = Val

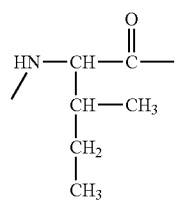

$R_4$ = Ile

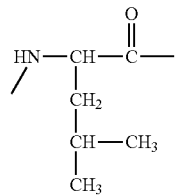

$R_4$ = Leu

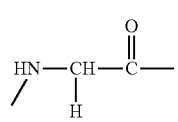

$R_4$ = Gly wherein the

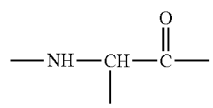

portion of the Tyr, 1-Nal, 2-Nal, Dab, Lys, Arg, Orn, (4NH$_2$) Phe, (3NH$_2$)Phe, Ser, Val, Ile, Leu, and Gly structures is of Scaffold 4.

7. A cyclic tetrapeptide having KOR antagonist and/or agonist activity, the cyclic tetrapeptide comprising one of cyclo[Trp-Ala-D-Pro-Phe], cyclo[Ala-Phe-D-Pro-Phe], cyclo[Trp-Phe-D-Pro-Ala], cyclo[Trp-Phe-N-Me-D-Ala-Phe], cyclo[Trp-Phe-Aib-Phe], cyclo[D-Trp-Ala-D-Pro-Phe], cyclo[D-Ala-Phe-D-Pro-Phe], cyclo[D-Trp-Phe-D-Pro-Ala], cyclo[D-Trp-Phe-NMeD-Ala-Phe], or a derivative thereof.

8. A cyclic tetrapeptide as in claim 7, wherein the cyclic tetrapeptide KOR antagonist is one of cyclo[Trp-Ala-D-Pro-Phe], cyclo[D-Trp-Ala-D-Pro-Phe], or derivative thereof.

9. A cyclic tetrapeptide as in claim 8, wherein the cyclic tetrapeptide KOR antagonist is cyclo[Trp-Ala-D-Pro-Phe], cyclo[D-Trp-Ala-D-Pro-Phe], or derivative thereof.

10. A cyclic tetrapeptide as in claim 7 having at least 3 times more KOR antagonist activity compared to CJ 15,208.

11. A pharmaceutical composition comprising:
a therapeutically effective amount of the cyclic tetrapeptide of claim 7.

12. A method for agonizing kappa-opioid receptors (KOR) present in tissue in vitro or in vivo, the method comprising:
administering at least one cyclic tetrapeptide KOR agonist to the tissue in an amount sufficient to agonize the KOR in the tissue, wherein the cyclic tetrapeptide KOR agonist is one of cyclo[Trp-Ala-D-Pro-Phe], cyclo[Ala-Phe-D-Pro-Phe], cyclo[Trp-Phe-D-Pro-Ala], cyclo[Trp-Phe-N-Me-D-Ala-Phe], cyclo[Trp-Phe-Aib-Phe], cyclo[D-Trp-Ala-D-Pro-Phe], cyclo[D-Ala-Phe-D-Pro-Phe], cyclo[D-Trp-Phe-D-Pro-Ala], cyclo[D-Trp-Phe-NMeD-Ala-Phe], or a derivative thereof.

13. A method for antagonizing kappa-opioid receptors (KOR) present in tissue in vitro or in vivo, the method comprising:
administering at least one cyclic tetrapeptide KOR antagonist to the tissue in an amount sufficient to antagonize the KOR in the tissue, wherein the cyclic tetrapeptide KOR antagonist is one of cyclo[Trp-Ala-D-Pro-Phe], cyclo[Ala-Phe-D-Pro-Phe], cyclo[Trp-Phe-D-Pro-Ala], cyclo[Trp-Phe-N-Me-D-Ala-Phe], cyclo[Trp-Phe-Aib-Phe], cyclo[D-Trp-Ala-D-Pro-Phe], cyclo[D-Ala-Phe-D-Pro-Phe], cyclo[D-Trp-Phe-D-Pro-Ala], cyclo[D-Trp-Phe-NMeD-Ala-Phe], or a derivative thereof.

14. A method as in claim 1, wherein the cyclic tetrapeptide KOR antagonist is one of cyclo[Trp-Ala-D-Pro-Phe], cyclo[D-Trp-Ala-D-Pro-Phe], or derivative thereof.

15. A method as in claim 14, wherein the cyclic tetrapeptide KOR antagonist is cyclo[Trp-Ala-D-Pro-Phe], cyclo[D-Trp-Ala-D-Pro-Phe], or derivative thereof.

16. A method as in claim 13, wherein the cyclic tetrapeptide KOR antagonist is selective for KOR over MOR or DOR.

17. A method as in claim 13, wherein the cyclic tetrapeptide KOR antagonist has at least about 3-fold more effectiveness compared to CJ 15,208 having the structure of Formula 1.

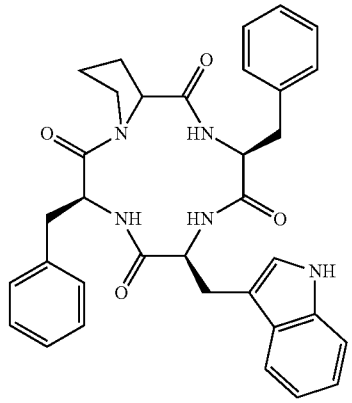

Formula 1

18. A method as in claim 13, wherein the tissue is located within a subject.

19. A method as in claim 18, wherein the cyclic tetrapeptide KOR antagonist is administered to a human subject having the tissue in an effective amount sufficient to cross the blood brain barrier and antagonize the KOR to provide a therapeutic effect.

20. A method as in claim 19, further comprising:
administering a therapeutically effective amount of the cyclic tetrapeptide KOR antagonist to a subject having the tissue for treating and/or inhibiting drug addiction, drug use, or drug seeking behavior in the subject.

21. A method as in claim 20, further comprising identifying the subject to have a history of drug addiction.

22. A method as in claim 20, wherein the drug is selected from cocaine, alcohol, amphetamines, methamphetamines, nicotine, opiate, or combinations thereof.

23. A method as in claim 20, wherein the administering is for treating and/or inhibiting drug seeking behavior and the drug seeking behavior is stress induced and/or a relapse.

24. A method as in claim 13, further comprising:
administering a therapeutically effective amount of the cyclic tetrapeptide KOR antagonist to a subject having the tissue for treating and/or inhibiting depression or anxiety.

* * * * *